US007818854B2

(12) United States Patent  (10) Patent No.: US 7,818,854 B2
Wilson  (45) Date of Patent: Oct. 26, 2010

(54) ULTRASOUND RADIATING MEMBERS FOR CATHETER

(75) Inventor: Richard R. Wilson, Seattle, WA (US)

(73) Assignee: Ekos Corporation, Bothell, WA (US)

( * ) Notice: Subject to any disclaimer, the term of this patent is extended or adjusted under 35 U.S.C. 154(b) by 0 days.

(21) Appl. No.: 12/371,544

(22) Filed: Feb. 13, 2009

(65) Prior Publication Data

US 2009/0144955 A1  Jun. 11, 2009

Related U.S. Application Data

(62) Division of application No. 11/143,518, filed on Jun. 2, 2005, now Pat. No. 7,509,715, which is a division of application No. 10/684,845, filed on Oct. 14, 2003, now Pat. No. 6,921,371.

(60) Provisional application No. 60/418,400, filed on Oct. 14, 2002.

(51) Int. Cl.
 *H04R 17/10* (2006.01)
(52) U.S. Cl. .......................... 29/25.35; 29/594; 29/847; 29/417; 310/368
(58) Field of Classification Search ................ 29/25.35, 29/594, 847, 852; 600/466; 601/2; 604/22; 310/320, 348, 368
See application file for complete search history.

(56) References Cited

U.S. PATENT DOCUMENTS

| 2,752,662 | A | * | 7/1956 | Crooks et al. ............... 29/25.35 |
| 2,961,382 | A | | 11/1960 | Singher et al. |
| 3,443,226 | A | | 3/1969 | Boyd |
| 3,565,062 | A | | 2/1971 | Kuris |
| 3,596,335 | A | * | 8/1971 | Bennett ..................... 29/25.35 |
| 4,027,659 | A | | 6/1977 | Slingluff |
| 4,040,414 | A | | 8/1977 | Suroff |
| 4,319,580 | A | | 3/1982 | Colley et al. |
| 4,354,502 | A | | 10/1982 | Colley et al. |

(Continued)

FOREIGN PATENT DOCUMENTS

DE  39 19 592 A1  2/1990

(Continued)

OTHER PUBLICATIONS

Akhtar, *Anti-HIV therapy with antisense oligonucleotides and ribozymes: realistic approaches or expensive myths?* (J. Antimicrob Chemother. 38(2): 159-165, 1996).

(Continued)

*Primary Examiner*—A. Dexter Tugbang
*Assistant Examiner*—David P Angwin
(74) *Attorney, Agent, or Firm*—Knobbe Martens Olson & Bear, LLP

(57) ABSTRACT

A method comprises providing a substantially planar slab of piezoelectric material having a top surface. The method further comprises drilling a plurality of holes through the top surface and into the slab. The method further comprises making a plurality of cuts through the top surface and into the slab. The cuts form a plurality of polygons that are generally centered about one of the holes. The method further comprises plating the slab with an electrically conductive material. The method further comprises removing the electrically conductive material from the top surface of the slab. The method further comprises cutting the slab substantially parallel to the top surface.

7 Claims, 25 Drawing Sheets

U.S. PATENT DOCUMENTS

| | | |
|---|---|---|
| 4,398,325 A | 8/1983 | Piaget et al. |
| 4,466,442 A | 8/1984 | Hilmann et al. |
| 4,512,762 A | 4/1985 | Spears |
| 4,531,943 A | 7/1985 | Van Tassel et al. |
| 4,573,470 A | 3/1986 | Samson et al. |
| 4,582,067 A | 4/1986 | Silverstein et al. |
| 4,628,223 A | 12/1986 | Takeuchi et al. |
| 4,657,543 A | 4/1987 | Langer et al. |
| 4,657,756 A | 4/1987 | Rasor et al. |
| 4,692,139 A | 9/1987 | Stiles |
| 4,698,058 A | 10/1987 | Greenfeld et al. |
| 4,710,192 A | 12/1987 | Liotta et al. |
| 4,750,902 A | 6/1988 | Wuchinich et al. |
| 4,762,915 A | 8/1988 | Kung et al. |
| 4,767,402 A | 8/1988 | Kost et al. |
| 4,772,594 A | 9/1988 | Hashimoto et al. |
| 4,774,958 A | 10/1988 | Feinstein |
| 4,780,212 A | 10/1988 | Kost et al. |
| 4,797,285 A | 1/1989 | Barenholz et al. |
| 4,808,153 A | 2/1989 | Parisi |
| 4,821,740 A | 4/1989 | Tachibana et al. |
| 4,844,882 A | 7/1989 | Widder et al. |
| 4,870,953 A | 10/1989 | Don Michael et al. |
| 4,877,031 A | 10/1989 | Conway et al. |
| 4,900,540 A | 2/1990 | Ryan et al. |
| 4,917,088 A | 4/1990 | Crittendon |
| 4,917,102 A | 4/1990 | Miller et al. |
| 4,920,954 A | 5/1990 | Alliger et al. |
| 4,924,863 A | 5/1990 | Sterzer |
| 4,936,281 A | 6/1990 | Stasz |
| 4,948,587 A | 8/1990 | Kost et al. |
| 4,953,565 A | 9/1990 | Tachibana et al. |
| 4,955,863 A | 9/1990 | Walker et al. |
| 4,971,991 A | 11/1990 | Umemura et al. |
| 4,992,257 A | 2/1991 | Bonnett et al. |
| 5,007,898 A | 4/1991 | Rosenbluth et al. |
| 5,021,044 A | 6/1991 | Sharawy |
| 5,040,537 A | 8/1991 | Katakura |
| 5,053,044 A | 10/1991 | Mueller et al. |
| 5,069,664 A | 12/1991 | Guess et al. |
| 5,081,993 A | 1/1992 | Kitney |
| 5,085,662 A | 2/1992 | Willard |
| 5,117,831 A | 6/1992 | Jang et al. |
| 5,149,319 A | 9/1992 | Unger |
| 5,156,050 A | 10/1992 | Schmid et al. |
| 5,158,071 A | 10/1992 | Umemura et al. |
| 5,163,421 A | 11/1992 | Bernstein et al. |
| 5,164,920 A | 11/1992 | Bast et al. |
| 5,181,920 A | 1/1993 | Mueller et al. |
| 5,190,766 A | 3/1993 | Ishihara |
| 5,197,946 A | 3/1993 | Tachibana |
| 5,209,720 A | 5/1993 | Unger |
| 5,215,680 A | 6/1993 | D'Arrigo |
| 5,216,130 A | 6/1993 | Line et al. |
| 5,250,034 A | 10/1993 | Appling et al. |
| 5,267,954 A | 12/1993 | Nita |
| 5,267,985 A | 12/1993 | Shimada et al. |
| 5,269,291 A | 12/1993 | Carter |
| 5,269,297 A | 12/1993 | Weng et al. |
| 5,277,913 A | 1/1994 | Thompson et al. |
| 5,279,546 A | 1/1994 | Mische et al. |
| 5,282,785 A | 2/1994 | Shapland et al. |
| 5,286,254 A | 2/1994 | Shapland et al. |
| 5,295,484 A | 3/1994 | Marcus et al. |
| 5,304,115 A | 4/1994 | Pflueger et al. |
| 5,315,998 A | 5/1994 | Tachibana et al. |
| 5,318,014 A | 6/1994 | Carter |
| 5,323,769 A | 6/1994 | Bommannan et al. |
| 5,324,255 A | 6/1994 | Passafaro et al. |
| 5,327,891 A | 7/1994 | Rammler |
| 5,328,470 A | 7/1994 | Nabel et al. |
| 5,342,292 A | 8/1994 | Nita et al. |
| 5,344,395 A | 9/1994 | Whalen et al. |
| 5,344,435 A | 9/1994 | Turner et al. |
| 5,345,940 A | 9/1994 | Seward et al. |
| 5,353,798 A | 10/1994 | Sieben |
| 5,354,279 A | 10/1994 | Hofling |
| 5,362,309 A | 11/1994 | Carter |
| 5,363,853 A | 11/1994 | Lieber |
| 5,368,036 A | 11/1994 | Tanaka et al. |
| 5,380,273 A | 1/1995 | Dubrul et al. |
| 5,390,678 A | 2/1995 | Gesswein et al. |
| 5,399,158 A | 3/1995 | Lauer et al. |
| 5,415,636 A | 5/1995 | Forman |
| 5,419,763 A | 5/1995 | Hildebrand |
| 5,421,338 A | 6/1995 | Crowley et al. |
| 5,423,797 A | 6/1995 | Adrian et al. |
| 5,431,663 A | 7/1995 | Carter |
| 5,445,155 A | 8/1995 | Sieben |
| 5,447,509 A | 9/1995 | Mills et al. |
| 5,458,568 A | 10/1995 | Racchini et al. |
| 5,465,726 A | 11/1995 | Dickenson et al. |
| 5,474,530 A | 12/1995 | Passafaro et al. |
| 5,474,531 A | 12/1995 | Carter |
| 5,489,279 A | 2/1996 | Meserol |
| 5,498,238 A | 3/1996 | Shapland et al. |
| 5,509,896 A | 4/1996 | Carter |
| 5,514,092 A | 5/1996 | Forman et al. |
| 5,520,189 A | 5/1996 | Malinowski et al. |
| 5,542,935 A | 8/1996 | Unger et al. |
| 5,558,092 A | 9/1996 | Unger et al. |
| 5,558,642 A | 9/1996 | Schweich, Jr. et al. |
| 5,567,687 A | 10/1996 | Magda et al. |
| 5,569,198 A | 10/1996 | Racchini |
| 5,580,575 A | 12/1996 | Unger et al. |
| 5,585,112 A | 12/1996 | Unger et al. |
| 5,586,982 A | 12/1996 | Abela |
| 5,588,962 A | 12/1996 | Nicholas et al. |
| 5,594,136 A | 1/1997 | Sessler et al. |
| 5,599,923 A | 2/1997 | Sessler et al. |
| 5,603,327 A | 2/1997 | Eberle |
| 5,606,974 A | 3/1997 | Castellano et al. |
| 5,609,574 A | 3/1997 | Kaplan et al. |
| 5,616,342 A | 4/1997 | Lyons |
| 5,617,851 A | 4/1997 | Lipkovker |
| 5,618,275 A | 4/1997 | Bock |
| 5,620,479 A | 4/1997 | Diederich |
| 5,628,728 A | 5/1997 | Tachibana et al. |
| 5,628,730 A | 5/1997 | Shapland |
| 5,630,837 A | 5/1997 | Crowley |
| 5,632,970 A | 5/1997 | Sessler et al. |
| 5,648,098 A | 7/1997 | Porter |
| 5,660,180 A | 8/1997 | Malinowski et al. |
| 5,663,327 A | 9/1997 | Tarabo et al. |
| 5,695,460 A | 12/1997 | Siegel et al. |
| 5,707,608 A | 1/1998 | Liu |
| 5,713,848 A | 2/1998 | Dubrul et al. |
| 5,718,921 A | 2/1998 | Mathiowitz et al. |
| 5,725,494 A | 3/1998 | Brisken |
| 5,733,572 A | 3/1998 | Unger et al. |
| 5,735,811 A | 4/1998 | Brisken |
| 5,766,902 A | 6/1998 | Craig et al. |
| 5,770,222 A | 6/1998 | Unger et al. |
| 5,776,429 A | 7/1998 | Unger et al. |
| 5,779,673 A | 7/1998 | Roth et al. |
| 5,817,048 A | 10/1998 | Lawandy |
| 5,836,896 A | 11/1998 | Rosenschein |
| 5,846,218 A | 12/1998 | Brisken et al. |
| 5,849,727 A | 12/1998 | Porter et al. |
| 5,876,989 A | 3/1999 | Berg et al. |
| 5,895,356 A | 4/1999 | Andrus |
| 5,895,398 A | 4/1999 | Wensel et al. |
| 5,916,192 A | 6/1999 | Nita et al. |
| 5,922,687 A | 7/1999 | Mann et al. |

| | | |
|---|---|---|
| 5,925,016 A | 7/1999 | Chornenky et al. |
| 5,938,595 A | 8/1999 | Glass et al. |
| 5,941,868 A | 8/1999 | Kaplan et al. |
| 5,997,497 A | 12/1999 | Nita et al. |
| 6,001,069 A | 12/1999 | Tachibana et al. |
| 6,024,718 A | 2/2000 | Chen et al. |
| 6,030,374 A | 2/2000 | McDaniel |
| 6,068,857 A | 5/2000 | Weitschies et al. |
| 6,078,830 A | 6/2000 | Levin et al. |
| 6,096,000 A | 8/2000 | Tachibana et al. |
| 6,096,070 A | 8/2000 | Ragheb et al. |
| 6,110,314 A | 8/2000 | Nix et al. |
| 6,113,558 A | 9/2000 | Rosenschein et al. |
| 6,117,858 A | 9/2000 | Porter et al. |
| 6,135,976 A | 10/2000 | Tachibana et al. |
| 6,176,842 B1 | 1/2001 | Tachibana et al. |
| 6,210,356 B1 | 4/2001 | Anderson et al. |
| 6,210,393 B1 | 4/2001 | Brisken |
| 6,228,046 B1 | 5/2001 | Brisken |
| 6,238,347 B1 | 5/2001 | Nix et al. |
| 6,245,747 B1 | 6/2001 | Porter et al. |
| 6,287,271 B1 | 9/2001 | Dubrul et al. |
| 6,295,990 B1 | 10/2001 | Lewis et al. |
| 6,296,619 B1 | 10/2001 | Brisken et al. |
| 6,312,402 B1 | 11/2001 | Hansmann |
| 6,346,098 B1 | 2/2002 | Yock et al. |
| 6,361,500 B1 | 3/2002 | Masters |
| 6,361,531 B1 | 3/2002 | Hissong |
| 6,372,498 B2 | 4/2002 | Newman et al. |
| 6,384,516 B1 | 5/2002 | Fraser |
| 6,416,740 B1 | 7/2002 | Unger |
| 6,425,853 B1 | 7/2002 | Edwards |
| 6,437,487 B1 | 8/2002 | Mohe et al. |
| 6,461,296 B1 | 10/2002 | Desai |
| 6,461,383 B1 | 10/2002 | Gesswein et al. |
| 6,503,204 B1 | 1/2003 | Sumanaweera et al. |
| 6,508,775 B2 | 1/2003 | McKenzie et al. |
| 6,508,816 B2 | 1/2003 | Shadduck |
| 6,524,251 B2 | 2/2003 | Rabiner et al. |
| 6,527,761 B1 | 3/2003 | Soltesz et al. |
| 6,548,047 B1 | 4/2003 | Unger |
| 6,551,337 B1 | 4/2003 | Rabiner et al. |
| 6,582,392 B1 | 6/2003 | Bennett et al. |
| 6,652,581 B1 | 11/2003 | Ding |
| 6,660,013 B2 | 12/2003 | Rabiner et al. |
| 6,680,301 B2 | 1/2004 | Berg et al. |
| 6,723,063 B1 | 4/2004 | Zhang et al. |
| 6,794,369 B2 | 9/2004 | Newman et al. |
| 6,921,371 B2 | 7/2005 | Wilson |
| 6,958,040 B2 | 10/2005 | Oliver et al. |
| 6,958,059 B2 | 10/2005 | Zadno-Azizi |
| 6,797,293 B2 | 12/2005 | Hansmann et al. |
| 7,141,044 B2 | 11/2006 | Gentsler |
| 2001/0003790 A1 | 6/2001 | Ben-Haim et al. |
| 2001/0007666 A1 | 7/2001 | Hoffman et al. |
| 2001/0053384 A1 | 12/2001 | Greenleaf et al. |
| 2002/0032394 A1 | 3/2002 | Brisken et al. |
| 2002/0055731 A1 | 5/2002 | Atala et al. |
| 2002/0068717 A1 | 6/2002 | Borrelli |
| 2002/0099356 A1 | 7/2002 | Unger et al. |
| 2002/0151792 A1 | 10/2002 | Conston et al. |
| 2003/0040501 A1 | 2/2003 | Newman et al. |
| 2003/0069525 A1 | 4/2003 | Brisken et al. |
| 2004/0015084 A1 | 1/2004 | Flesch et al. |
| 2004/0024347 A1 | 2/2004 | Wilson et al. |
| 2004/0034306 A1 | 2/2004 | Seward |
| 2004/0039329 A1 | 2/2004 | Ueberle |
| 2004/0106841 A1 | 6/2004 | Shaw et al. |
| 2005/0027247 A1 | 2/2005 | Carrison et al. |
| 2005/0091833 A1 * | 5/2005 | Kiepen et al. ............... 29/594 |
| 2005/0197619 A1 | 9/2005 | Rule et al. |
| 2007/0265560 A1 | 11/2007 | Soltani et al. |

FOREIGN PATENT DOCUMENTS

| | | | |
|---|---|---|---|
| DE | 40 05 743 | 8/1991 | |
| EP | 0 189 329 | 7/1986 | |
| EP | 0 529 675 | 8/1992 | |
| EP | 0 629 382 | 11/1993 | |
| EP | 668052 A2 | 2/1995 | |
| EP | 1 252 885 | 10/2002 | |
| JP | 61048984 * | 3/1986 | ............... 29/594 |
| JP | 2-180275 | 7/1990 | |
| WO | WO 89/05160 | 6/1989 | |
| WO | WO 91/09629 | 7/1991 | |
| WO | WO 92/07622 | 5/1992 | |
| WO | WO 93/08738 | 5/1993 | |
| WO | WO 94/05361 | 3/1994 | |
| WO | WO 95/01751 | 1/1995 | |
| WO | WO 95/15118 | 6/1995 | |
| WO | WO 96/07432 | 3/1996 | |
| WO | WO 96/15815 | 5/1996 | |
| WO | WO 96/27341 | 9/1996 | |
| WO | WO 96/29935 | 10/1996 | |
| WO | WO 96/35469 | 11/1996 | |
| WO | WO 96/36286 | 11/1996 | |
| WO | WO 97/19645 | 6/1997 | |
| WO | WO 98/11826 | 3/1998 | |
| WO | WO 89/04142 | 5/1998 | |
| WO | WO 98/48711 | 11/1998 | |
| WO | WO 98/58699 | 12/1998 | |
| WO | WO 99/25385 | 5/1999 | |
| WO | WO 99/33500 | 7/1999 | |
| WO | WO 99/34858 | 7/1999 | |
| WO | WO 99/39738 | 8/1999 | |
| WO | WO 00/38580 | 7/2000 | |
| WO | WO 01/53009 | 7/2001 | |
| WO | WO 03/007649 | 1/2003 | |

OTHER PUBLICATIONS

Anderson, *Human gene therapy*. (Nature 392:25-30, 1998).
Bao, et al. "Transfection of a Reporter Plasmid into Cultured Cells by Sonoporation in Vitro," Ultrasound in Med. and Biol., vol. 23, No. 6, pp. 953, 1997.
Bleeker et al., J. Ultrasound, Med. 9(8): 461-71 (Aug. 1990) On the Application of Ultrsonic Contrast Agents for Blood Flowmetry and Assessment of Cardiac Perfusion.
Branch, *A Good Antisense Molecule is Hard to Find*, (Trends in Biochem Sci 23: 45-50, 1998).
B.D. Butler, J. clin. Ultrasound 14(5): 408-12 (Jun. 1986) Production of Microbubbles for Use as Echo Contrast Agents.
Cancer Letters, vol. 72, 1993, pp. 195-199.
Cancer Letters, vol. 78 (1-3), 1994, pp. 177-181.
Crooke, *Basic Principles of Antisense Therapeutics* (Springer-Verlag, Eds, New York, 1998, pp. 1 and 4).
Fechmeier, et al. "Transfection of Mammalian Cells with Plasid DNA by Scrape Loading and Sonication Loading," Proc. Natl. Acad. Sci. USA, vol. 84, pp. 8463-8467, Dec. 1987.
Feinstein et al., J. Am. Coll. Cardiol. 3(1): 14-20 (Jan. 1984) Two-dimensional Contrast Echocardiography I. In Vitrro Development and Quantitative Analysis of Echo Contrast Agents.
Feldman, et al. "Optimal Techniques for Arterial Gene Transfer," Cardiovascular Research, 35 (1997) pp. 391-404.
Greenleaf, William J. et al.; Artifical Cavitation Nuclei Significantly Enhance Acoustically Induced Cell Transfection. vol. 24, No. 4 pp. 587-595, 1998.
Ho and Parkinson, *Antisense Oigonucleoties and Therapeutics for Malignant Diseases*, (Seminars in Drug Discovery 24(2): 187-202, 1997).
Holland, C.K. and R.E. Apfel, J. Acoust. Soc. Am. 88(5): 2059-2069 (Nov. 1990) Thresholds for Transient Cavitation Produced by Pulsed Ultrsound in a Controlled Nuclei Environment.
Hynynen et al.; "Small Cylindrical Ultrasound Sources Fro Induction of Hyperthermia via Body Cavities or Interstitial Implants"; *Arizona*

Cancer Center and Department of Radiation Oncology, University of Arizona Health Sciences Center; vol. 9, No. 2; pp. 263-274; 1993.
Japanese Journal of Cancer Research, vol. 81, No. 3, Mar. 1990, pp. 304-308.
Jeffers, Russel et al; Dimethylformamide as an Enhancer of Cavitation-Induced Cell Lysis In Vitro, vol. 97, No. 1, Jan. 1995.
Jeffers, R.J. et al.; Evaluation of the Effect of Cavitation Activity on Drug-Ultrsound Synergisms, 1993.
Keller et al., J. Ultrasound Med. 5(9): 493-8 (Sep. 1986) Automated Production and Analysis of Echo Contrast Agents.
Kim, et al. "Ultra-sound Mediated Transfection of Mammalian Cells," Human Gene Therapy, 7: 1339-1346 (Jul. 10, 1996).
Kim, T.F. Medical news & Perspectives, JAMA 261(11): 1542 (Mar. 17, 1989) Microbubbles Show Promise for Enhancing Ultrasound Signal, Image, Other Applications.
Kotnis, et al. "Optimisation of Gene Transfer into Vascular Endothelial Cells Using Electroporation," Eur J. Vasc Surg, 9, 71-79 (1995).
Lang et al., Circulation 75(1): 229-234 (Jan. 1987) Contrast Ultrasonography of the Kidney: a New Method for Evaluation of Renal Perfusion in Vivo.
Lee et al.; "Arrays of Mulielement Ultrasound Applicators For Interstitial Hyperthermia"; *IEEE Transactions on biomedical Engineering*; vol. 46, No. 7; Jul. 1999.
Leong et al., Biomaterials, vol. 7: 364-371 (Sep. 1986) Polyanhydrides for Controlled Release of Bioactive Agents.
G. Maywald et al., "Experience With Atraumatic Vascular Diagnosis With the Aid of the Ultrasonic Doppler Technique", Electromedica, vol. 2 pp. 43-48 (1976).
Meltzer et al., J. Clin. Ultrasound 8(2): 121-7 (Apr. 1980) The Source of Ultrsound Contrast Effect.
Miller, Douglas L. et al.; Sonoporation of Cultured Cells in the Rotation Tube Exposure System, vol. 25, No. 1, 1999.
Orkin and Motulsky, *Report and Recommendations of the Panel to Assess the NIH Investment in Research on Gene Therapy*, (p. 1-38, Dec. 7, 1995).
PCT Search Report, PCT Application PCT/US2006/13531; Apr. 12, 2006.
Porter, et al "Interaction of Diagnostic Ultrasound with Synthetic Olionucleotide-Labeled Perfluorcarbon-Exposed Sonicated Dextrose Albumin Microbubbles," J Ultrasound Med, 15:557-584, 1996.
Porter, T.R. et al., Thrombolytic Enhancement With Perfluorocarbom-Exposed Sonicated Dextrose Albumin Microbubbles, Nov. 1996.
Prat, F. et al.; In Vivo Effects of Cavitation Alone or in Combination Wity Chemotherapy in a Peritoneal Carinomatosis in the Rat. vol. 68, pp. 13-17, 1993.
Price, Richard et al.; Delivery of Colloidal Particles and Red Blood Cells to Tissue Through Microvessel Ruptures Created by Targeted Microbubble Destruction With Ultrasound, Sep. 29, 1998.
Romano et al., *Latest Developments in Gene Transfer Technology: Achievements, Perspectives, and Controversies over Therapeutice Applications*, (Stem Cells 18: 19-39, 2000).
Rosenschein, U. et al., Experimental Ultrasonic Angioplasty: Disruption of Atherosclerotic Plaques and Thrombi in Vitro and Arterial Recanalization in, 1990.
Somia and Verma, *Gene Therapy: Trials and Tribulations*, (Nature Reviews Genetics 1:91-99, 2000).
Tachibana, K. "Enhancement of Fibrinolysis with Ultrasound Energy", JVIR, vol. 3, No. 2, May 1992, pp. 299-303.
Tachibana K.; Albumin Microbubble Echo-Contrast Materials as an Enhancer for Ultrasound Accelerated Thrombolysis, Sep. 1, 1995.
Tsurumi, et al. "Direct Intramuscular Gene Transfer of Naked DNA Encoding Vascular Endothelial Growth Factor Augments Collateral Development and Tissue Perfusion," Circulation, 1996; 94: 3281-3290.
Unger, et al. "Ultrasound Enhances Gene Expression of Liposomal Transfection," Investigative Radiology, vol. 32, No. 12, pp. 723-727, 1997.
Unger, Evan C. et al.; Acoustically Active Liposheres Containing Paclitaxel, vol. 11, No. 12, 1992.
Vandenburg et al., Am. Heart J., 115(4), 733-9 (Apr. 1988) Myocardial Risk Area and Peak Gray Level Measurement by Contrast Echocardiography: Effecct of Microbubble Size and Concentration, Injection Rate, and Coronary Vasodilation.
Verma et al., *Gene Therapy—promises, problems and prospects*, (Nature 389: 239-242, 1997).
Wheatly et al., Biomaterials 11(19): 713-7 (Nov. 1990) Contrast Agents for Diagnostic Ultrsound: Development and Evaluation of Polymer-Coated Microbubbles.
Wu, Yunqiu et al., Binding as Lysing of Blood Clots Using MRX-408, May 1998.
Wyber, et al. "The Use of Sonication for the Efficient Delivery of Plasmid DNA into Cells," Pharmaceutical Research, vol. 14, No. 6, pp. 750-756, 1997.
PCT Search Report, PCT Application PCT/US2008/86713; Dec. 12, 2008.

* cited by examiner

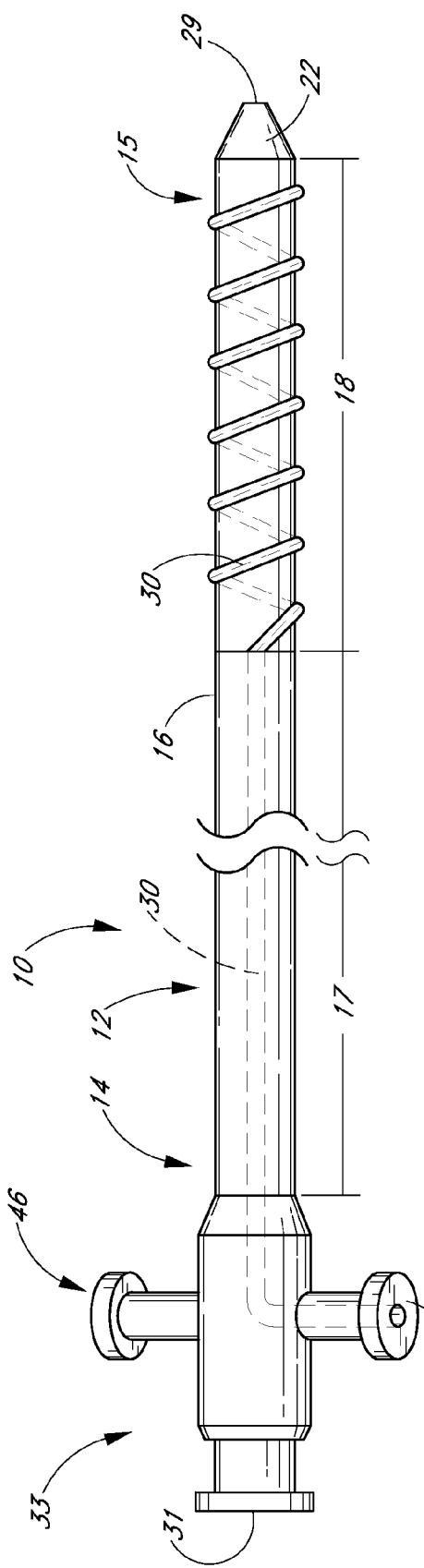
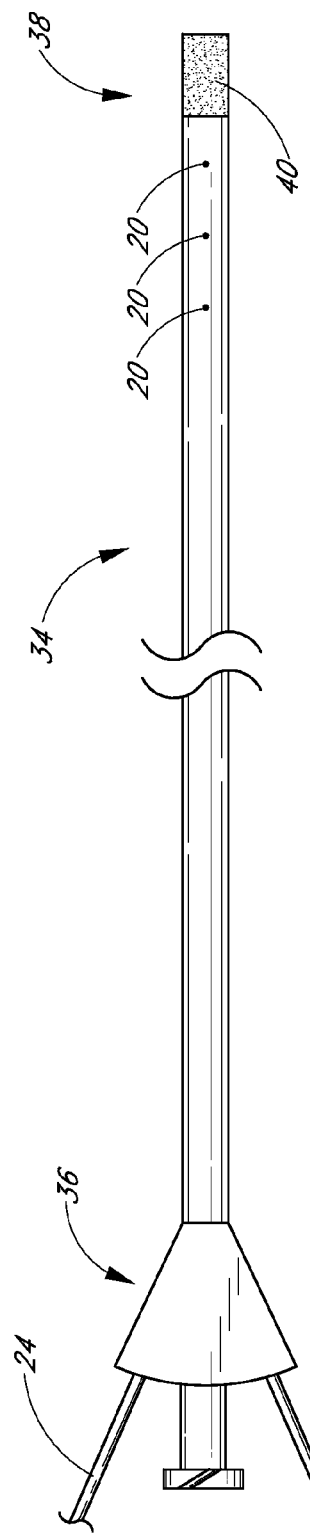
FIG. 3A
FIG. 3B

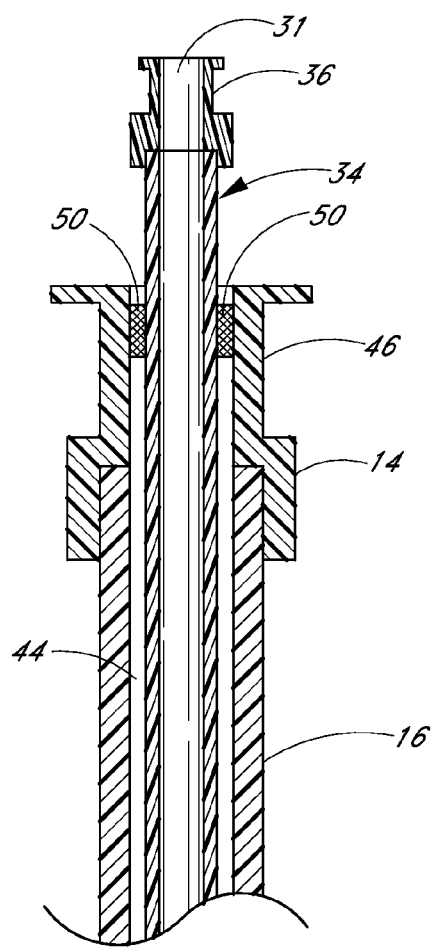
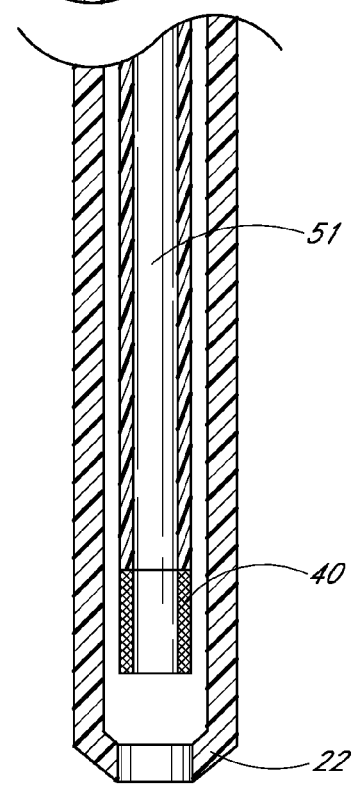
FIG. 4C

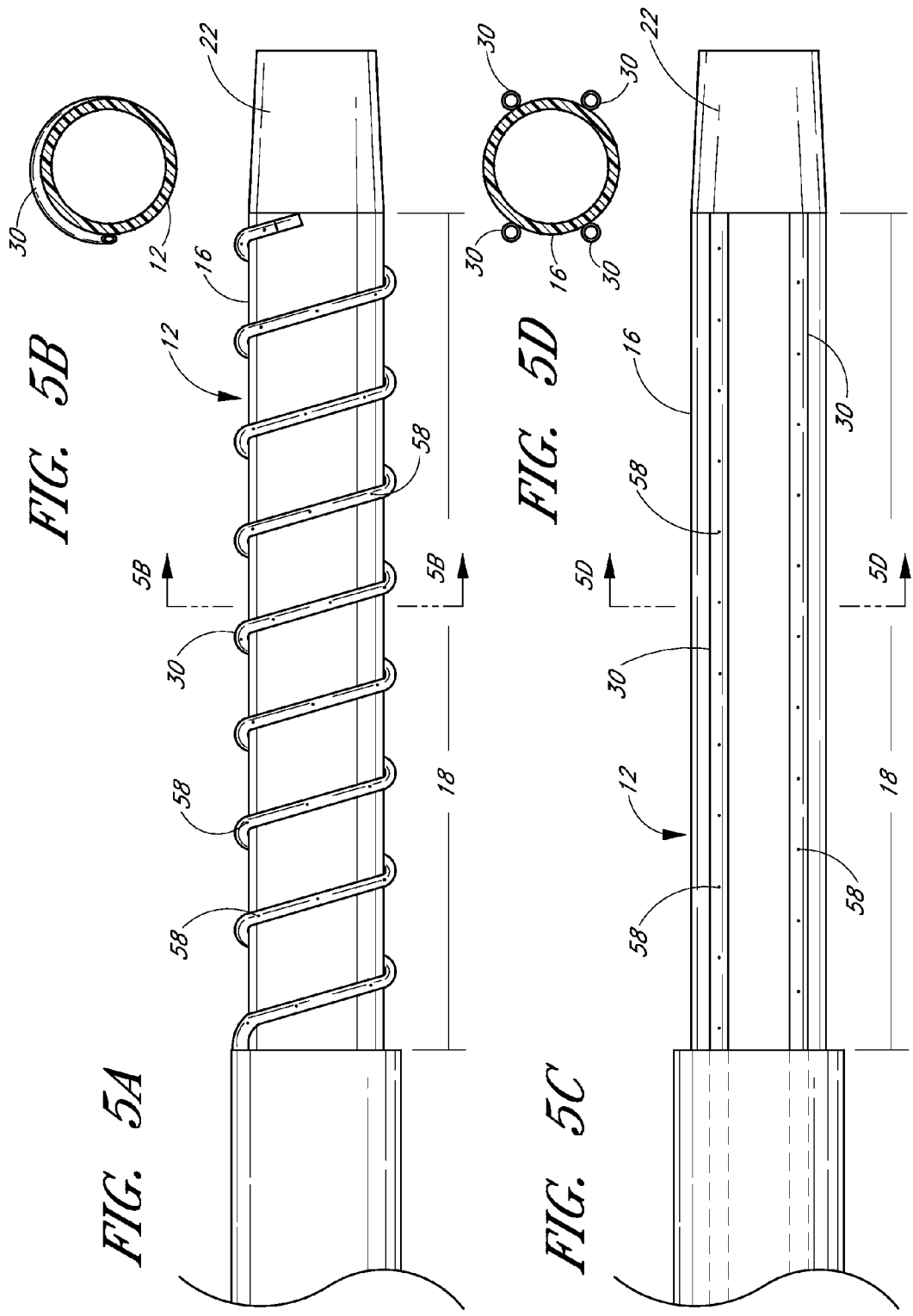

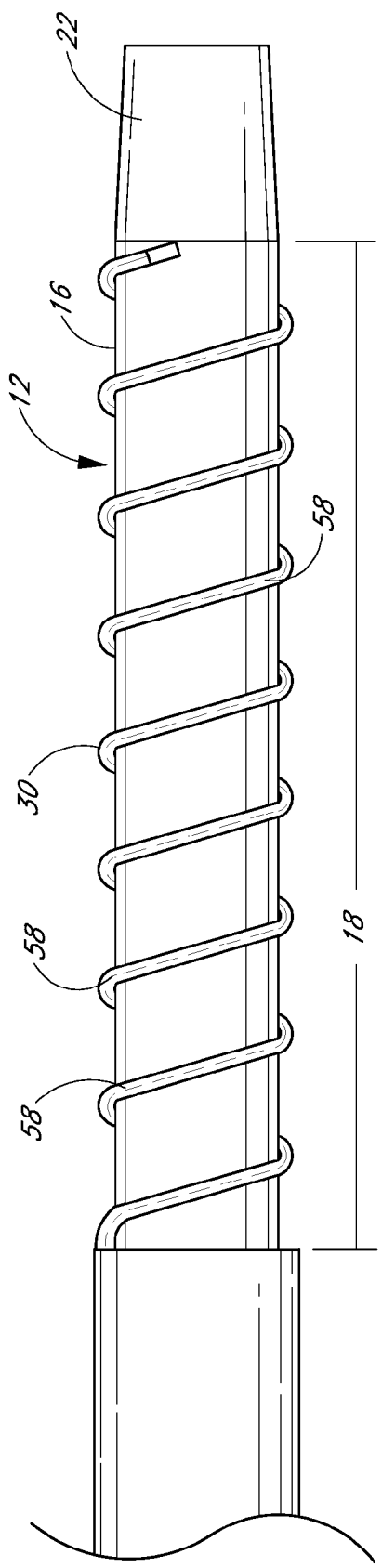
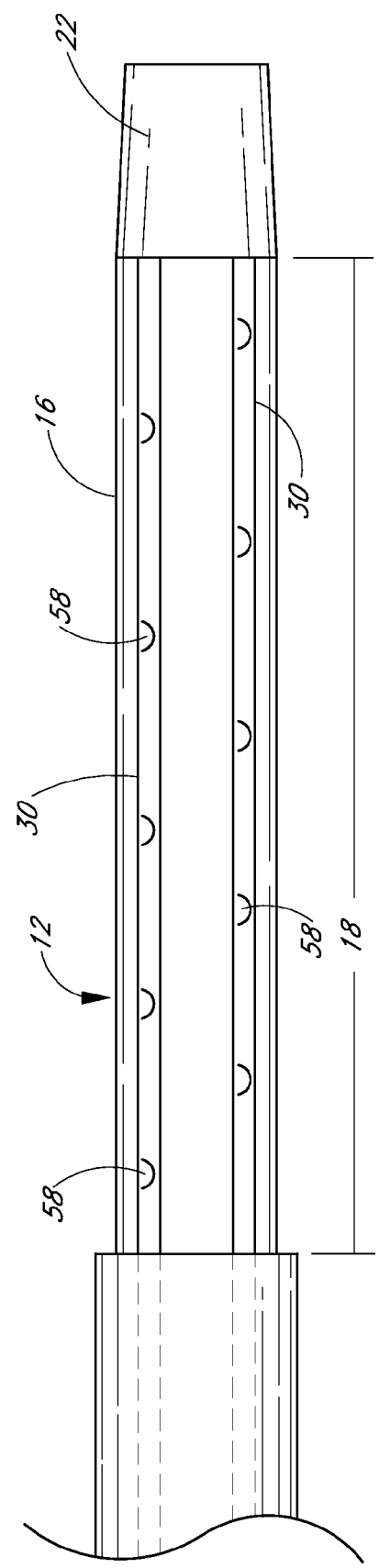

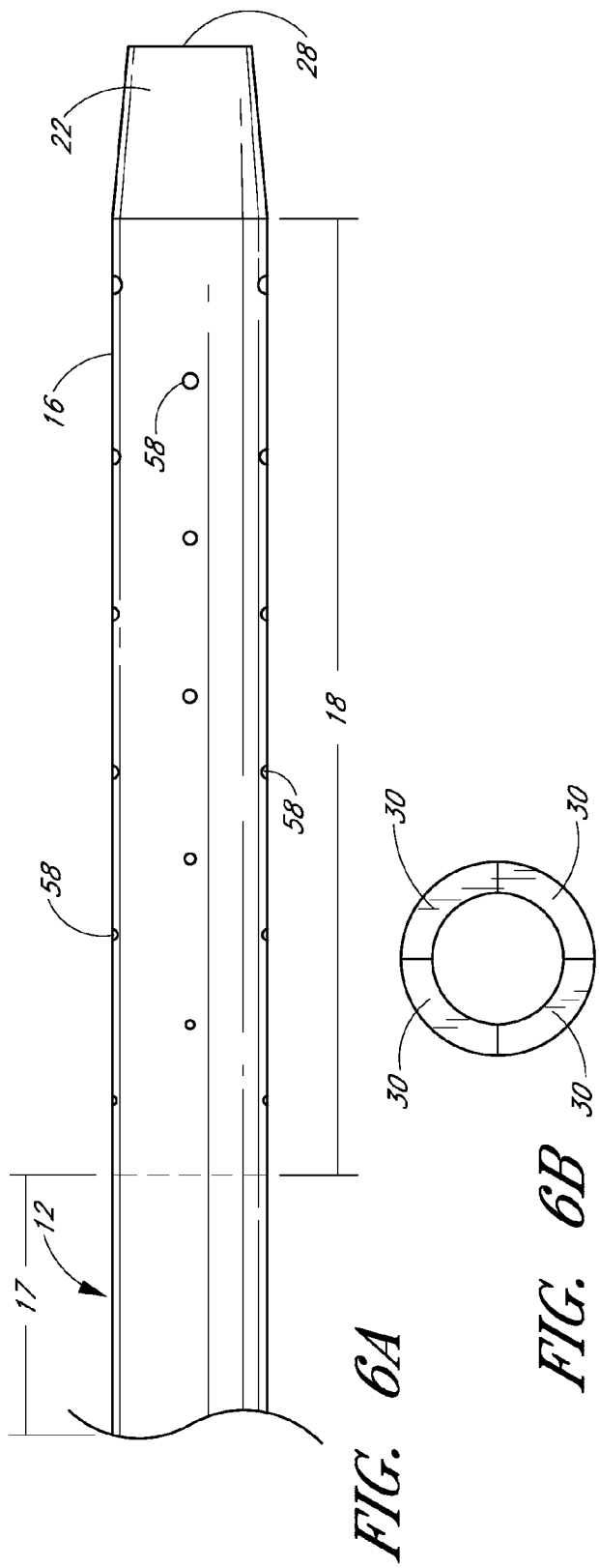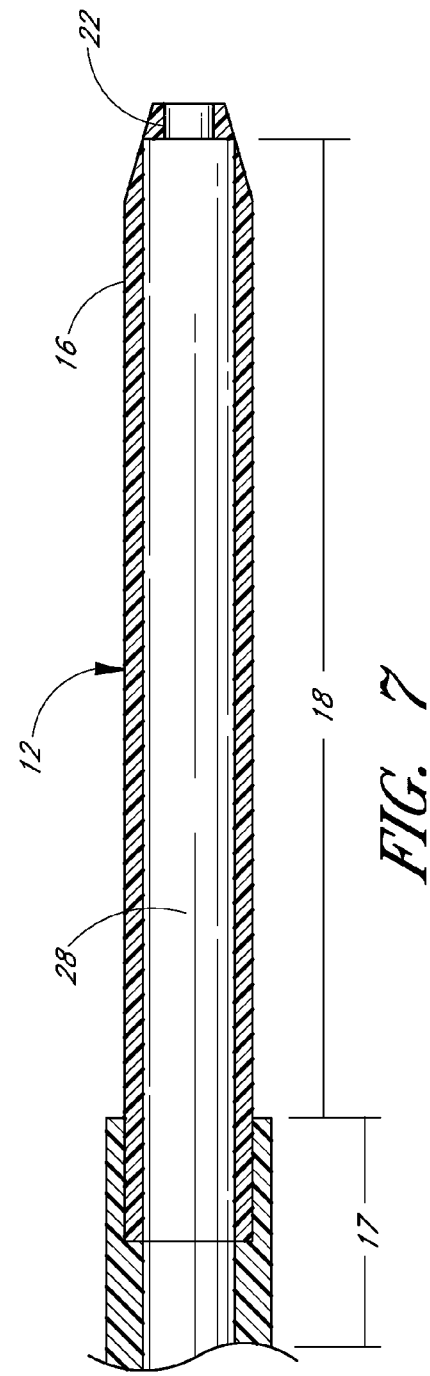

ULTRASOUND RADIATING MEMBERS FOR CATHETER

PRIORITY APPLICATION

This application is a divisional of U.S. patent application Ser. No. 11/143,518 (filed Jun. 2, 2005), which is a divisional of U.S. patent application Ser. No. 10/684,845 (filed 14 Oct. 2003) now U.S. Pat. No. 6,921,371, which claims the benefit of U.S. Provisional Patent Application 60/418,400 (filed 14 Oct. 2002). All of these priority applications are hereby incorporated by reference herein in their entirety.

FIELD OF THE INVENTION

The present invention relates generally to ultrasound radiating members, and relates more specifically to ultrasound radiating members configured for use in medical applications to enhance the delivery and/or effect of a therapeutic compound.

BACKGROUND OF THE INVENTION

Several therapeutic and diagnostic applications in the medical field use ultrasonic energy. For example, ultrasonic energy can be used to enhance the delivery and/or effect of various therapeutic compounds. See, for example, U.S. Pat. Nos. 4,821,740, 4,953,565 and 5,007,438. In some applications, a catheter delivers ultrasonic energy and a therapeutic compound to a specific treatment site within the body. Such a catheter typically includes an ultrasonic assembly for generating the ultrasonic energy and a delivery lumen for delivering the therapeutic compound to the treatment site. Using this device, sometimes referred to as an "ultrasonic catheter," the ultrasonic energy can be applied at the treatment site to enhance the therapeutic effect and/or the delivery of the therapeutic compound.

Ultrasonic catheters have successfully been used to treat human blood vessels that have become occluded or completely blocked by plaque, thrombi, emboli or other substances that reduce the blood carrying capacity of the vessel. See, for example, U.S. Pat. No. 6,001,069. To remove the blockage, solutions containing dissolution compounds can be delivered directly to the blockage site using an ultrasonic catheter. In this design, ultrasonic energy generated by the catheter enhances the delivery and/or therapeutic effect of the dissolution compounds.

Ultrasonic catheters can also be used to perform gene therapy on an isolated region of a body lumen. For example, as disclosed in U.S. Pat. No. 6,135,976, an ultrasonic catheter can be provided with one or more expandable sections for occluding a section of the body lumen. A gene therapy composition can then be delivered to the occluded section through a delivery lumen. Ultrasonic energy is then delivered to the occluded section to enhance the entry of the gene therapy composition into the cells of the occluded section.

Another use for an ultrasonic catheter is the delivery and activation of light activated drugs, as disclosed in U.S. Pat. No. 6,176,842. Additionally, ultrasound-enhanced thrombolytic therapy can be used to dissolve blood clots in arteries and veins in the treatment of conditions such as peripheral arterial occlusion and deep vein thrombosis. In such applications, an ultrasonic catheter delivers ultrasonic energy into a vessel, where the ultrasonic energy enhances thrombolysis with agents such as urokinase, tissue plasminogen activator ("TPA") and others.

SUMMARY OF THE INVENTION

Conventional ultrasonic assemblies include one or more ultrasound radiating members, which usually have a cylindrical or rectangular geometry. Cylindrical ultrasound radiating members are often difficult to manufacture and can be subject to mechanical failure. Rectangular ultrasound radiating members are easier to manufacture but Applicant has determined that they produce a less radially uniform distribution of ultrasound energy Thus, an ultrasound radiating member having an improved manufacturing process, improved durability and with a more radially uniform distribution of ultrasound energy has been developed.

In accordance with one embodiment of the present invention, an ultrasound radiating member comprising a front face and a rear face. Each face has n sides, wherein n is greater than 4. The ultrasound radiating member further comprises n faces connecting the sides of the front and rear faces. The ultrasound radiating member further comprises a central bore extending from the front face to the rear face.

In accordance with another embodiment of the present invention, an ultrasound catheter comprises a tubular member. the ultrasound catheter further comprises at least one ultrasound radiating member positioned with the tubular member. The ultrasound radiating member comprises a front face and a rear face. Each face has n sides, wherein n is greater than 4. The ultrasound radiating member further comprises n faces connecting the sides of the front and rear faces. the ultrasound radiating member further comprises a central bore extending from the front face to the rear face. At least a portion of the surfaces of the inner bore and n faces are coated with a conductive material. The ultrasound catheter further comprises a first wire and a second wire. The first wire is connected to the inner bore, and the second wire is connected to at least one of the n faces.

In accordance with another embodiment of the present invention, a method for manufacturing an ultrasonic radiating member comprises providing a sheet of piezoelectric material. The method further comprises drilling a plurality of holes into the piezoelectric material. Each hole has an inner surface. The method further comprises making a plurality of cuts into the sheet. Each cut has a depth less than the depth of the holes. The cuts form an elongate polygon that is generally centered about one of the holes. The polygon has an outer surface. The method further comprises plating at least a portion of the inner and outer surfaces with a conductive material. The method further comprises cutting a backside from the sheet so as to separate individual elongate polygons.

In accordance with another embodiment of the present invention, an apparatus comprises an elongate ultrasound radiating member having a hollow, cylindrical central core and three or more substantially flat sides. The apparatus further comprises a first cylindrical electrode applied to the hollow, cylindrical central core. The apparatus further comprises a second electrode applied to at least one of the sides.

In accordance with another embodiment of the present invention, a method comprises providing a substantially planar slab of piezoelectric material having a top surface. The method further comprises drilling a plurality of holes through the top surface and into the slab. The method further comprises making a plurality of cuts through the top surface and into the slab. The cuts form a plurality of polygons that are generally centered about one of the holes. The method further comprises plating the slab with an electrically conductive material. The method further comprises removing the electrically conductive material from the top surface of the slab. The method further comprises cutting the slab substantially parallel to the top surface.

BRIEF DESCRIPTION OF THE DRAWINGS

Exemplary embodiments of the ultrasound radiating members disclosed herein, and certain applications therefor, are illustrated in the accompanying drawings, which are for illustrative purposes only. The drawings comprise the following figures, in which like numerals indicate like parts.

FIG. 3A is side elevation view of one embodiment of an ultrasonic catheter which is particularly well-suited for treating long segment peripheral arterial occlusions, such as those occasionally found in the arteries of the leg.

FIG. 3B is a side elevation view of an inner core configured for use with the ultrasonic catheter of FIG. 3A.

FIG. 4C is a cross-sectional view of another modified embodiment of an ultrasonic catheter.

FIG. 5A is a side view of the distal end of the ultrasonic catheter of FIG. 3A.

FIG. 5B is a cross-sectional view of the distal end of the ultrasonic catheter of FIG. 5A taken through line 5B-5B.

FIG. 5C is a side view of a modified embodiment of the distal end of an ultrasonic catheter.

FIG. 5D is a cross-sectional view of the distal end of the ultrasonic catheter of FIG. 5C taken along line 5D-5D.

FIG. 5E is a side view of another modified embodiment of the distal end of an ultrasonic catheter.

FIG. 5F is a side view yet of another modified embodiment of the distal end of an ultrasonic catheter.

FIG. 6A is a side view of yet another modified embodiment of the distal end of an ultrasonic catheter which includes drug delivery ports of increasing size.

FIG. 6B is a cross-sectional view of the distal end of an ultrasonic catheter wherein the proximal and distal ends are made of different materials.

FIG. 7 is a cross-sectional view of a distal end of an ultrasonic catheter that includes an integral occlusion device.

DETAILED DESCRIPTION OF PREFERRED EMBODIMENTS

Introduction

Figure 1:
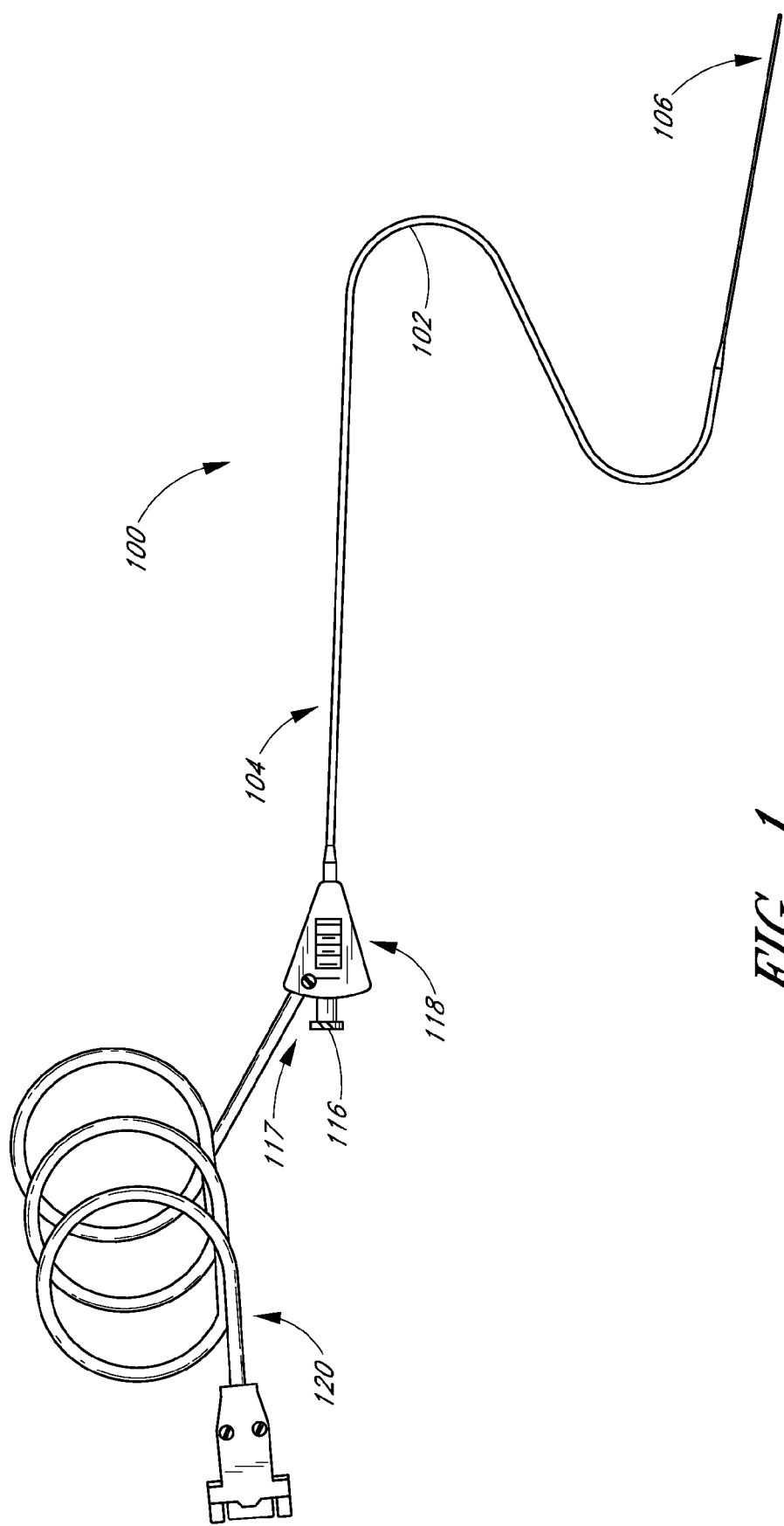
FIG. 1 is a side view of an ultrasonic catheter that is particularly well-suited for use in small vessels of the distal anatomy.

Certain exemplary embodiments described herein relate to ultrasonic catheters and methods of using ultrasonic catheters. As described above, ultrasonic catheters can be used to enhance the effect and/or delivery of a therapeutic compound. As used herein, the term "therapeutic compound" refers, in addition to its ordinary meaning, to drugs, biological macromolecules (including, but not limited to, proteins and nucleic acids), and other pharmacological agents, including combinations thereof. Exemplary applications of ultrasonic catheters are provided in U.S. Pat. Nos. 5,318,014, 5,362,309, 5,474,531, 5,628,728, 6,001,069, and 6,210,356.

In one exemplary embodiment, an ultrasonic catheter is adapted for use in the treatment of thrombus in the small blood vessels or arteries of the human body, such as, for example, the small cerebral arteries. In another embodiment, an ultrasonic catheter is adapted for use in the treatment of thrombus in larger blood vessels or arteries of the human body such as those located in the lower leg. In still other embodiments, the ultrasonic catheters disclosed herein can also be used in other therapeutic applications, such as performing gene therapy (see, for example, U.S. Pat. No. 6,135,976), activating light activated drugs used to cause targeted tissue death (see, for example, U.S. Pat. No. 6,176,842) and causing cavitation to produce biological effects (see, for example, U.S. Pat. No. RE36,939). Moreover, such therapeutic applications may be used in various human tissues, such as other parts of the circulatory system, solid tissues, duct systems and body cavities. Certain embodiments of the ultrasonic catheters disclosed herein can also be used in other medical applications, such as diagnostic and imaging applications.

In exemplary embodiments, the ultrasonic catheters disclosed herein can be used in applications where the ultrasonic energy provides a therapeutic effect by itself. For example, in certain applications, ultrasonic energy can provide and/or reduce stenosis and/or restenosis; tissue ablation, abrasion or disruption; promotion of temporary or permanent physiological changes in intracellular or intercellular structures; and/or rupture of micro-balloons or micro-bubbles for therapeutic compound delivery. See, for example, U.S. Pat. Nos. 5,269,291 and 5,431,663. The methods and apparatuses disclosed herein can also be used in applications that do not require the use of a catheter, such as, enhancement of hyperthermic drug treatment, use of externally generated ultrasonic energy to enhance the effect and/or delivery of a therapeutic compound at a specific site within the body, and use of ultrasonic energy to provide a therapeutic or diagnostic effect by itself. See, for example, U.S. Pat. Nos. 4,821,740, 4,953,565, 5,007,438 and 6,096,000.

The term "ultrasonic energy" is used broadly, and encompasses its ordinary definition, as well as mechanical energy transferred through longitudinal pressure or compression waves with a frequency greater than about 20 kHz and less than about 20 MHz. In one embodiment, the waves have a frequency between about 500 kHz and 20 MHz, and in another embodiment the waves have a frequency between about 1 MHz and 3 MHz. In yet another embodiment, the waves have a frequency of about 3 MHz.

The term "catheter" is used broadly, and encompasses its ordinary definition, as well as flexible tubes configured to be inserted into a body cavity, duct or vessel.

Overview of a Small Vessel Ultrasonic Catheter

Figure 2A:
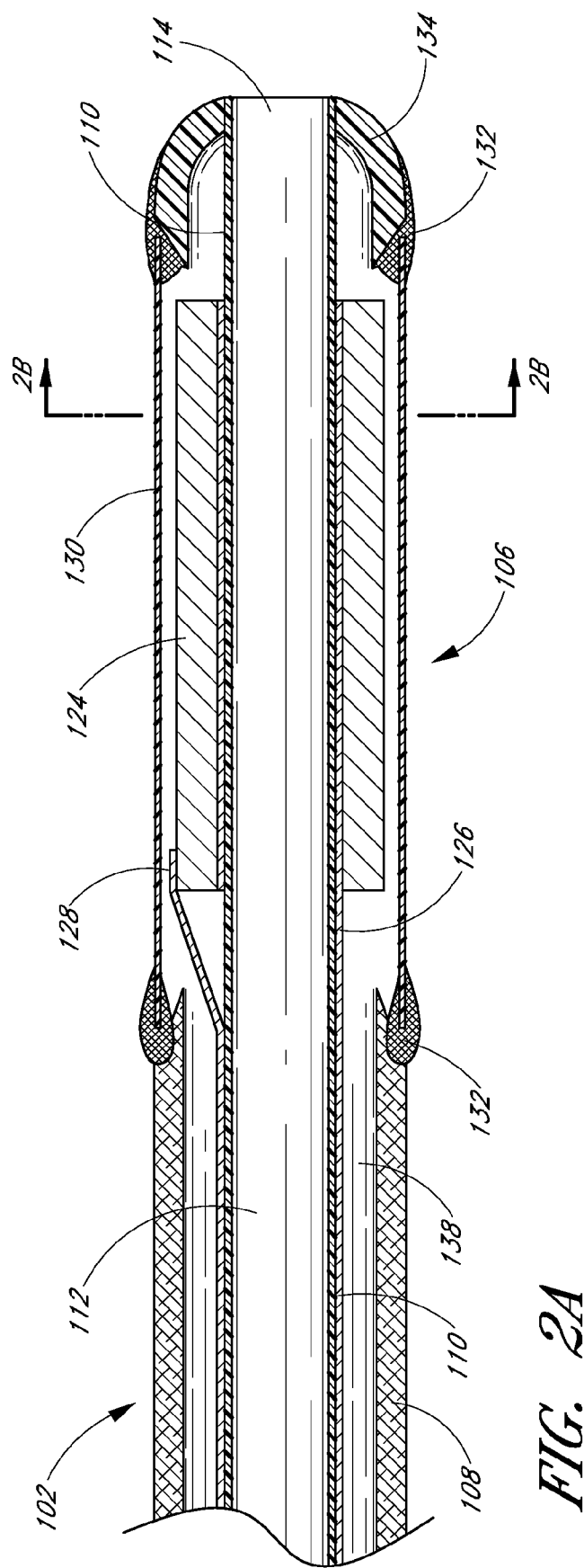
FIG. 2A is a cross-sectional view of the distal end of the ultrasonic catheter of FIG. 1.
Figure 2B:
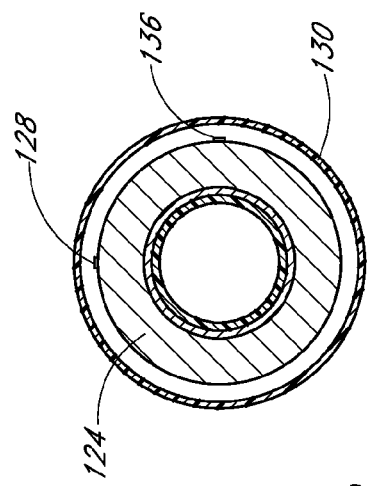
FIG. 2B is a cross-sectional view of the ultrasonic catheter of FIG. 2A taken through line 2B-2B.

FIGS. 1, 2A and 2B illustrate an exemplary embodiment of an ultrasonic catheter 100 that is particularly well-suited for use in small vessels of the distal anatomy, such as in small neurovascular vessels in the brain.

As illustrated in FIGS. 1 and 2A, the ultrasonic catheter 100 generally comprises a multi-component tubular body 102 having a proximal end 104 and a distal end 106. The tubular body 102 and other components of the catheter 100 can be manufactured in accordance with conventional catheter manufacturing techniques. Suitable dimensions can be readily selected based on the dimensions of the treatment site and the desired percutaneous access site.

In an exemplary embodiment, the tubular body 102 is elongate and flexible, and comprises an outer sheath 108 (illustrated in FIG. 2A) that is positioned over an inner core 110. For example, in embodiments particularly well-suited for small neurovascular vessels, the outer sheath 108 can comprise extruded polytetrafluoroethylene ("PTFE"), polyetheretherketone ("PEEK"), polyethylene ("PE"), polymides, braided polymides and/or other similar materials. In such embodiments, the outer sheath 108 has an outer diameter of approximately 0.039 inches at its proximal end and between approximately 0.033 and approximately 0.039 inches at its distal end. In such embodiments, the outer sheath 108 has an axial length of approximately 150 centimeters. In other embodiments, the outer sheath 108 can be formed from a braided tubing comprising high or low density polyethylenes, urethanes, nylons, and so forth. Such configurations enhance the flexibility of the tubular body 102. In still other embodiments, the outer sheath 108 can include a stiffening member (not shown) at the tubular body proximal end 104.

The inner core 110 at least partially defines a central lumen 112, or "guidewire lumen," which preferably extends through the length of the catheter 100. The central lumen 112 has a distal exit port 114 and a proximal access port 116. As best illustrated in FIG. 1, the proximal access port 116 is defined by therapeutic compound inlet port 117 on a back end hub 118, which is attached to the outer sheath proximal end 104. In the exemplary embodiment illustrated in FIG. 1, the back end hub 118 is attached to a control box connector 120, which described in greater detail below.

In an exemplary embodiment, the central lumen 112 is configured to receive a guidewire (not shown) having a diameter of between approximately 0.010 includes to approximately 0.012 inches. In an exemplary embodiment, the inner core 110 is formed from polymide or a similar material, which can optionally be braided to increase the flexibility of the tubular body 102.

Referring now to the exemplary embodiment illustrated in FIGS. 2A and 2B, the distal end 106 of the tubular body 102 includes an ultrasound radiating member 124. In the illustrated embodiment, the ultrasound radiating member 124 comprises an ultrasonic transducer, which converts, for example, electrical energy into ultrasonic energy.

In the embodiment illustrated in FIGS. 2A and 2B, the ultrasound radiating member 124 is in the shape of a hollow cylinder as is conventional in the prior art. Improved radiating members 124 will be described in FIGS. 12 through 17 below.

The inner core 110 extends through the ultrasound radiating member 124, which is positioned over the inner core 110. The ultrasound radiating member 124 can be secured to the inner core 110 in a suitable manner, such as with an adhesive. Extending the core through the member 124 advantageously provides enhanced cooling of the ultrasound radiating member 124. Specifically, as will be explained in more detail below, a therapeutic compound can be injected through the central lumen 112, thereby providing a heat sink for heat generated by the ultrasound radiating member 124.

As described above, suitable operating frequencies for the ultrasound radiating member 124 include, but are not limited to, from about 20 kHz to less than about 20 MHz. In one embodiment, the frequency is between about 500 kHz and about 20 MHz, and in another embodiment the frequency is between about 1 MHz and about 3 MHz. In yet another embodiment, the ultrasonic energy has a frequency of about 3 MHz.

In the exemplary embodiment illustrated in FIGS. 2A and 2B, ultrasonic energy is generated by supplying electrical power to the ultrasound radiating member 124. The electrical power can be supplied through the controller box connector 120, which is connected to a first electrically conductive wire 126 and a second electrically conductive wire 128. As illustrated, the wires 126, 128 extend through the catheter body 102. In such embodiments, the wires 126, 128 are secured to the inner core 110, lay along the inner core 110 and/or extend freely in the space between the inner core 110 and the outer sheath 108. In the illustrated arrangement, the first wire 126 is connected to the hollow center of the ultrasound radiating member 124, while the second wire 128 is connected to the outer periphery of the ultrasound radiating member 124. In an exemplary embodiment, the ultrasound radiating member 124 comprises a piezoelectric ceramic oscillator; in other embodiments, the ultrasound radiating member 124 comprises other similar materials.

In the modified embodiment, the catheter 10 may include more than one ultrasound radiating member 124. In such an embodiment, the ultrasound radiating members may be electronically connected in series or parallel as described above and in more detail below.

Still referring to the exemplary embodiment illustrated in FIGS. 2A and 2B, the distal end of the catheter 100 includes sleeve 130, which is generally positioned about the ultrasound radiating member 124. In such embodiments, the sleeve 130 comprises a material that readily transmits ultrasonic energy. Suitable materials for the sleeve 130 include, but are not limited to, polyolefins, polyimides, polyesters and other low ultrasound impedance materials. Low ultrasound impedance materials are materials that readily transmit ultrasonic energy with minimal absorption of the ultrasonic energy. The proximal end of the sleeve 130 can be attached to the outer sheath 108 with an adhesive 132. In a similar manner, the distal end of the sleeve 130 can be attached to a catheter tip 134. In the illustrated arrangement, the tip 134 is generally rounded and is also attached to the distal end of the inner core 110.

In an exemplary embodiment, the tubular body 102 is divided into at least three sections of varying stiffness. The first section, which includes the proximal end 104, is generally more stiff than a second section, which lies between the proximal end 104 and the distal end 106. This arrangement facilitates the movement and placement of the catheter 100 within small vessels. The third section, which includes ultrasound radiating element 124, is generally stiffer than the second section due to the presence of the ultrasound radiating element 124.

Stilling referring to the exemplary embodiment illustrated in FIG. 2B, the catheter 100 includes at least one temperature sensor 136 that is located at or near the distal end of the catheter 100, and near the ultrasound radiating member 124. Suitable temperature sensors include, but are not limited to, diodes, thermistors, thermocouples, resistance temperature detectors ("RTD"), and fiber optic temperature sensors that use thermalchromic liquid crystals. In an exemplary embodiment, the temperature sensors are operatively connected to a control box (not shown) through a control wire that extends through the tubular body 102 and back end hub 118, and that is operatively connected to a control box through the control box connector 120. In such embodiments, the control box includes a feedback control system, such as the control system described herein. In an exemplary embodiment, the control box is configured to monitor and control the power, voltage, current and phase of the signal supplied to the ultrasound radiating members 124. This configuration allows the temperature of the catheter to be monitored and controlled.

In an exemplary use, a free end of a guidewire is percutaneously inserted into the arterial system at a suitable insertion site. The guidewire is advanced through the vessels towards a treatment site, which includes, for example, a clot. In an exemplary embodiment, the guidewire is directed through the clot.

The catheter 100 is then percutaneously inserted through the insertion site and advanced along the guidewire towards the treatment site using conventional over-the-guidewire techniques. The catheter 100 is advanced until the distal end of the catheter 100 is positioned at or within the clot. In a modified embodiment, the catheter distal end includes radiopaque markers to aid in positioning the catheter at the treatment site.

The guidewire is then withdrawn from the central lumen 112. A therapeutic compound solution source (not shown), such as a syringe with a Luer fitting, is attached to the therapeutic compound inlet port 117 and the control box connector 120 is connected to the control box. Thus, the therapeutic compound can be delivered through the central lumen 112 and the exit port 114 to the clot. Suitable therapeutic compounds for treating thrombus include, but are not limited to, aqueous solutions containing a thrombolytic agent (that is, a clot-dissolving drug), such as, heparin, urokinase, streptokinase, TPA and BB-10153, which is manufactured by British Biotech (Oxford, United Kingdom). In other embodiments, wherein the ultrasonic catheter is not used to remove a thrombus, other agents can be delivered through the central lumen. Such other agents include, but are not limited to, cancer treating drugs, genetic material, light activated drugs, and so forth.

The ultrasound radiating member 124 is activated to deliver ultrasonic energy through the distal end of the catheter 100 to the treatment site. As mentioned above, suitable frequencies for the ultrasound radiating member 124 include, but are not limited to, from about 20 kHz to less than about 20 MHz. In one embodiment, the frequency is between about 500 kHz and about 20 MHz, and in another embodiment the frequency is between about 1 MHz and about 3 MHz. In yet another embodiment, the ultrasonic energy has a frequency of about 3 MHz. The therapeutic compound and ultrasonic energy can be applied until the clot is partially or entirely dissolved. Once the clot has been dissolved to the desired degree, the catheter 100 can be withdrawn from the treatment site.

In a modified embodiment, the catheter 100 includes a cooling system for removing heat generated by the ultrasound radiating member 124. In one such embodiment, a return path can be formed in region 138, such that coolant from a coolant system can be directed through region 138 (see FIG. 2A).

Overview of a Long Segment Ultrasonic Catheter

FIGS. 3A and 3B illustrate one embodiment of an ultrasonic catheter 10, which is particularly well-suited for treating long segment peripheral arterial occlusions, such as those occasionally found in the arteries of the leg.

As illustrated in FIG. 3A, the ultrasonic catheter 10 generally comprises a multi-component tubular body 12 having a proximal end 14 and a distal end 15. The tubular body 12 and other components of the catheter 10 can be manufactured in accordance with any of a variety of conventional catheter manufacturing techniques. Suitable dimensions for the catheter components can be readily selected based on the natural and anatomical dimensions of the treatment site and of the desired percutaneous insertion site.

In an exemplary embodiment, the tubular body 12 is elongate and flexible, and comprises an outer sheath 16. The outer sheath 16 preferably includes a support section 17 located at the proximal end and an energy delivery section 18 located at the distal end of the catheter 10. In one embodiment, the support section 17 comprises extruded PTFE, PEEK, PE and/or similar materials that provide the outer sheath 16 with enough flexibility, kink resistance, rigidity and structural support necessary to push the energy delivery section 18 to a treatment site. In an embodiment particularly well-suited for treating thrombus in the arteries of the leg, the outer sheath 16 has an outside diameter of approximately 0.060 inches to approximately 0.075 inches. In such, an embodiment, the outer sheath 16 has an axial length of approximately 90 centimeters.

In an exemplary embodiment, the energy delivery section 18 of the outer sheath 16 comprises a relatively thin material compared to the support section 17. A thinner material advantageously increases the acoustic transparency of the energy delivery section 18. Suitable materials for the energy delivery section 18 include, but are not limited to, high or low density polyethylenes, urethanes, nylons, and so forth.

Figure 3C:
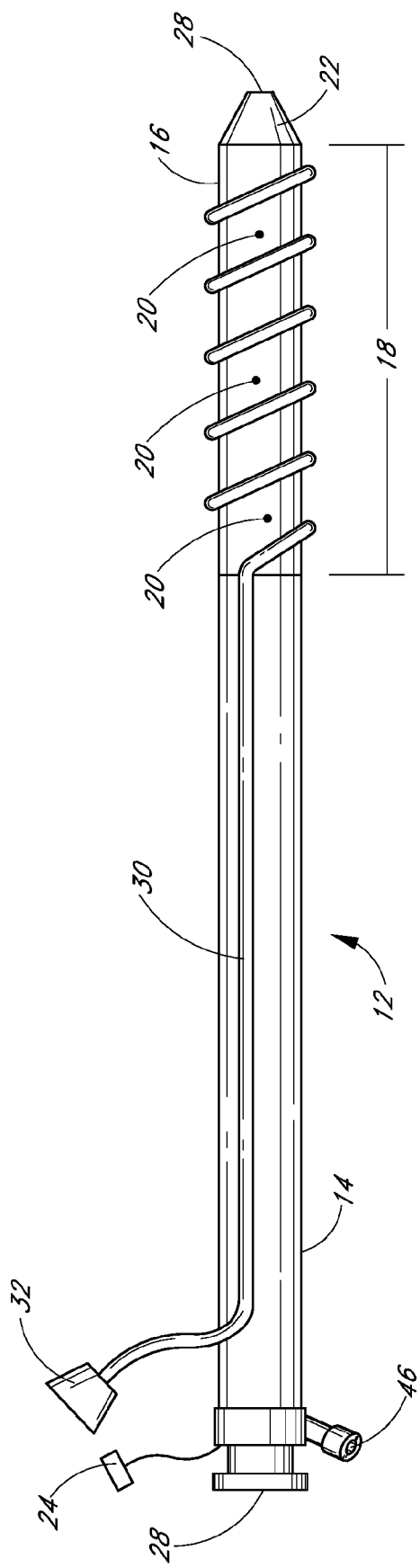
FIG. 3C is a side elevation view of a modified embodiment of an ultrasonic catheter.

Referring now to the exemplary embodiments illustrated in FIGS. 3A and 3C, the outer sheath 16 defines a utility lumen 28 that extends through the length of the catheter 10. In the exemplary embodiment illustrated in FIG. 3A, the utility lumen 28 has a distal exit port 29 and a proximal access port 31. The proximal access port 31 is defined by a backend hub 33, which is attached to the proximal end of the outer sheath 16.

Still referring to FIG. 3A, a delivery lumen 30 is positioned adjacent the energy delivery section 18. The delivery lumen 30 includes an inlet port 32, which is formed in the backend hub 33 and is coupled to a therapeutic compound source via a hub such as a Luer type fitting. The delivery lumen 30 can be incorporated into the support section 17 (as illustrated in FIG. 3A) or can be external to the support section (as illustrated in FIG. 3C).

The catheter 10 also includes an elongated inner core 34 (see FIG. 3B) having a proximal end 36 and a distal end 38. An ultrasound radiating member 40 is positioned at or near the core distal end 38. Further information regarding methods and structures for mounting ultrasound radiating members within the inner core can be found in Applicant's co-pending U.S. patent application Ser. No. 10/309,388, which is hereby incorporated herein by reference in its entirety. For example, in an exemplary embodiment, a plurality of ultrasound radiating members, such as the ultrasound radiating members disclosed herein and illustrated in FIGS. 12 through 17, can be mounted within the inner core. In such embodiments, the ultrasound radiating members can be electrically connected in series or in parallel.

Figure 4A:
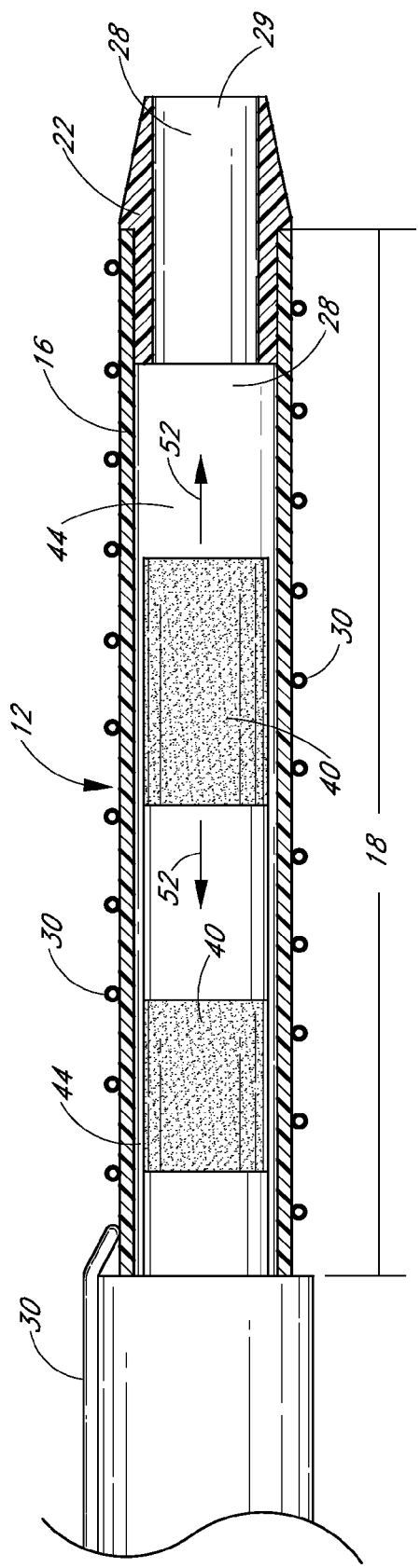
FIG. 4A is a cross-sectional view of a distal end of the ultrasonic catheter of FIG. 3A.

The inner core 34 has an outer diameter which permits the inner core 34 to be inserted into the utility lumen 28 via the proximal access port 31. FIG. 4A illustrates the inner core 34 inserted inside the utility lumen 28 with an ultrasound radiating member 40 is positioned within the energy delivery section 18. Suitable outer diameters of the inner core 34 include, but are not limited to, between approximately 0.010 inches and approximately 0.100 inches. Suitable diameters of the utility lumen 28 include, but are not limited to between approximately 0.015 inches and approximately 0.110 inches.

The ultrasound radiating member 40 can be rotated or moved within the energy delivery section 18 as illustrated by the arrows 52 in FIG. 4A. The ultrasound radiating member 40 can be moved within the energy delivery section 18 by manipulating the inner core proximal end 36 while holding the backend hub 33 stationary. The inner core 34 is at least partially constructed from a material that provides enough structural support to permit movement of the inner core 34 within the outer sheath 16 without causing the outer sheath 16 to kink. Suitable materials for the inner core 34 include, but are not limited to, polyimides, polyesters, polyurethanes, thermoplastics, elastomers, and braided wires with fiber reinforcement.

As illustrated in FIG. 4A, the outer diameter of the inner core 34 can be smaller than the inner diameter of the utility lumen 28, thereby creating a cooling fluid lumen 44 between the inner core 34 and the utility lumen 28. A cooling fluid can flow through the cooling fluid lumen 44, past the ultrasound radiating members 40 and through the distal exit port 29. Cooling fluid can be supplied via a cooling fluid fitting 46 provided on the backend hub 33 shown in FIG. 3A. The cooling fluid flow rate and/or the power to the ultrasound radiating members 40 can be adjusted to maintain the temperature of the ultrasound radiating member 40 within a specified range.

Figure 4B:
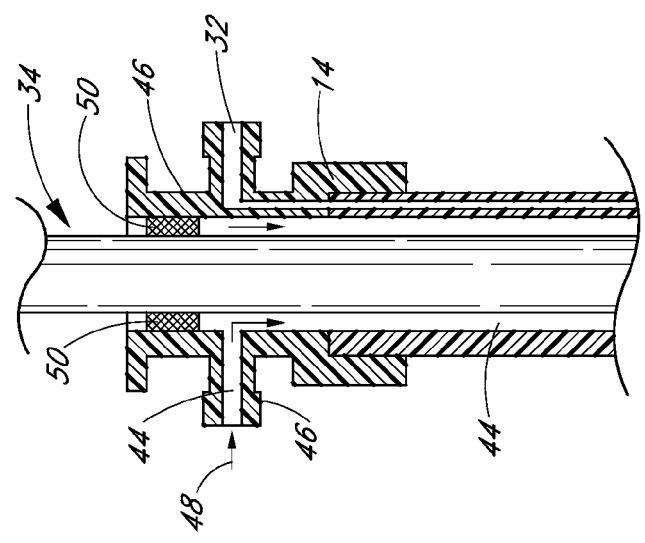
FIG. 4B is a cross-sectional view of a proximal end of the ultrasonic catheter of FIG. 3A.

Referring now to FIG. 4B, the cooling fluid can be flowed from the cooling fluid fitting 46 through the cooling fluid lumen 44 as illustrated by arrows 48. The cooling fluid fitting 46 optionally includes a hemostasis valve 50 having an inner diameter that substantially matches the diameter of the inner core 34. The matched diameters reduce leaking of the cooling fluid between the cooling fluid fitting 46 and the inner core 34.

Referring now to the exemplary embodiment illustrated in FIG. 4C, the ultrasound radiating member 40 comprises a hollow cylinder, and the inner core 34 defines a central lumen 51, which extends through the ultrasound radiating member 40. In such embodiments, the cooling fluid flows through the central lumen 51, and past and through the ultrasound radiating member 40, thereby providing cooling to the ultrasound radiating member 40. In this configuration, the cooling fluid can be supplied via the proximal access port 31, with the cooling fluid fitting 46 and hemostasis valve 50 providing a seal between the inner core 34 and the outer sheath 16. In modified embodiments, the sheath 16 can be closed at the catheter distal end, thereby providing a system for recirculating cooling fluid, and for preventing cooling fluid from entering the patient's vascular system.

Referring again to the exemplary embodiment illustrated in FIG. 3A, the catheter 10 includes an occlusion device 22 positioned at the distal end of the catheter 10. In such embodiments, the utility lumen 28 extends through the occlusion device 22. The portion of the utility lumen 28 extending through the occlusion device 22 has a diameter that can accommodate a guidewire (not shown) but that prevents the ultrasound radiating member 40 from passing through the occlusion device 22. Suitable inner diameters for the occlusion device 22 include, but are not limited, to between approximately 0.005 inches and approximately 0.050 inches.

Referring now to the exemplary embodiment illustrated in FIG. 5A, the delivery lumen 30 includes a therapeutic compound delivery portion that is positioned adjacent the energy delivery section 18. As illustrated in FIG. 5B, in an exemplary embodiment, the delivery lumen 30 is wound around the tubular body 12 in the energy delivery section 18. In such embodiments, the delivery lumen 30 includes a series of delivery ports 58. A therapeutic compound source coupled to the inlet port 32 can provide a pressure which drives the therapeutic compound through the delivery lumen 30 and out the delivery ports 58. A suitable material for the delivery lumen 30 includes, but is not limited to, high or low density polyethylenes, urethanes, nylons, and so forth.

In modified embodiments, the catheter 10 can include a plurality of delivery lumens 30. The delivery lumens 30 can be wound around the energy delivery section 18 or they can be positioned along the length of the energy delivery section 18 as illustrated in FIGS. 5C and 5D. Each delivery lumen 30 can be coupled to the same drug inlet port 32, or each delivery lumen 30 can be coupled to an independent drug inlet port 32, thus allowing different therapeutic compound solutions to be delivered to different delivery ports 58.

In an exemplary embodiment, the delivery ports 58 are positioned close enough to achieve a substantially even flow of therapeutic compound solution around the circumference of the energy delivery section 18, and along the length of the energy delivery section 18. The proximity of adjacent delivery ports 58 can be changed by changing the density of delivery ports 58 along the delivery lumen 30, by changing the number of windings of the delivery lumen 30 around the energy delivery section 18, or by changing the number of delivery lumens 30 positioned along the energy delivery section 18. In one embodiment, the windings of the delivery lumens 30 has a pitch that ranges from about one spiral per one centimeter to about one spiral per 20 centimeters.

The size of the delivery ports 58 can be the same or can vary along the length of the delivery lumen 30. For example, in one embodiment, the size of the delivery ports 58 along the distal portion of the energy delivery section 18 are larger than the delivery ports 58 along the proximal portion of the energy delivery section 18. The increase in size of the delivery ports 58 can be configured to produce similar flow rates of therapeutic compound solution through each delivery port 58. A similar flow rate increases the uniformity of therapeutic compound solution flow rate along the length of the outer sheath 16. In one embodiment in which the delivery ports 58 have similar sizes along the length of the delivery lumen 30, the delivery ports 58 have a diameter of between approximately 0.0005 inches and approximately to 0.0050 inches. In another embodiment in which the size of the delivery ports 58 changes along the length of the delivery lumen 30, the delivery ports 58 have a diameter of between approximately 0.0001 inches and approximately 0.005 inches at the proximal end and between about 0.0005 inches and approximately 0.020 inches at the distal end. The increase in size between adjacent delivery ports 58 can be substantially uniform between along the delivery lumen 30. The dimensional increase of the delivery ports 58 can be dependent upon the material and the diameter of the delivery lumen 30. The delivery ports 58 can be punched, drilled, burnt with a laser, and so forth, into the delivery lumen 30.

Uniformity of the drug solution flow along the length of the outer sheath 16 can also be increased by increasing the density of the delivery ports 58 toward the distal end of the delivery lumen 30. Additionally, the delivery ports 58 can be slits with a straight shape (as illustrated in FIG. 5E) or an arcuate shape (as illustrated in FIG. 5F). The delivery lumen 30 can be constructed from materials such as polyimide, nylon, Pebax®, polyurethane or silicon. When the delivery lumen 30 contains drug solution, the slits remain closed until the pressure within the delivery lumen 30 exceeds a threshold pressure, where the pressure on each of the slit-shaped delivery ports 58 is approximately uniform. Once the threshold pressure is exceeded, the slit-shaped delivery ports 58 will open almost simultaneously, resulting in a nearly uniform flow of therapeutic compound solution from the slits. When the pressure in the delivery lumen 30 falls below the threshold pressure, the slit-shaped delivery ports 58 close and prevent delivery of additional therapeutic compound solution. Generally, the stiffer the material used to construct the delivery lumen 30, the higher the threshold pressure at which the slit-shaped delivery ports 58 will open. The slit shape can also prevent the delivery ports 58 from opening when exposed to low pressures from outside the outer sheath 16. As a result, slit shaped delivery ports 58 can enhance control of therapeutic compound delivery.

In the embodiment illustrated in FIG. 6A, the outer sheath 16 and energy delivery section 18 are constructed from a single material. Suitable materials include, but are not limited to, high or low density polyethylenes, urethanes, nylons, and so forth. The entire outer sheath 16, or only the outer sheath proximal end, can be reinforced by braiding, mesh or other constructions to increase the ability of the catheter to be pushed through a patient's vasculature ("pushability"). As illustrated in FIG. 6A, the delivery ports 58 can be incorporated into the outer sheath 16. The delivery ports 58 can be coupled with independent delivery lumens 30 formed within the outer sheath 16, as illustrated in FIG. 6B.

In the exemplary embodiment illustrated in FIG. 7, the outer sheath 16 includes a support section 17 that is constructed from a different material than the energy delivery section 18. As mentioned above, the energy delivery section 18 can be constructed from a material which readily transmits ultrasound energy. The support section 17 can be constructed from a material which provides structural strength and kink resistance. Further, the support section 17, or the proximal end of the support section 17, can be reinforced by braiding, mesh or other constructions to increase kink resistance and pushability. Suitable materials for the support section 17 include, but are not limited to PTFE, PEEK, PE and/or similar materials. Suitable outer diameters for the support section 17 include, but are not limited to between approximately 0.020 inches and approximately 0.200 inches. Suitable materials for the energy delivery section 18 include, but are not limited to high or low density polyethylenes, urethanes, nylons, and other materials that produce minimal ultrasound attenuation. Such materials readily transmit ultrasound energy with minimal absorption of the ultrasound energy. FIG. 7 also illustrates an occlusion device 22 that is integrally formed with the energy delivery section 18.

Electrical Specifications

The foregoing electrical specification relate generally to both small vessel and long segment ultrasonic catheter. In the exemplary embodiments disclosed herein, the ultrasound radiating members comprise ultrasonic transducers configured to convert, for example, electrical energy into ultrasonic energy. An exemplary ultrasonic transducer for generating ultrasonic energy from electrical energy includes is a piezoelectric ceramic oscillator. In a modified embodiment, the ultrasonic energy can be generated by an ultrasonic transducer that is remote from the ultrasound radiating members, and the ultrasonic energy can be transmitted to the ultrasound radiating members via a wire, for example.

In an exemplary embodiment, the ultrasound radiating members comprise an ultrasonic transducer with a cylindrical shape. In other embodiments, the ultrasonic transducer can be a block, a hollow cylinder or a disk. The ultrasound radiating members can optionally be positioned concentrically around the inner core 34. In a modified embodiment, the ultrasound radiating members are formed of an array of smaller ultrasound radiating members. Similarly, a single ultrasound radiating member can be formed a combination of several smaller ultrasound radiating members.

As mentioned previously, suitable operating frequencies for the ultrasound radiating members include, but are not limited to, from about 20 kHz to less than about 20 MHz. In one embodiment, the frequency is between about 500 kHz and about 20 MHz, and in another embodiment the frequency is between about 1 MHz and about 3 MHz. In yet another embodiment, the ultrasonic energy has a frequency of about 3 MHz.

Figure 8A:
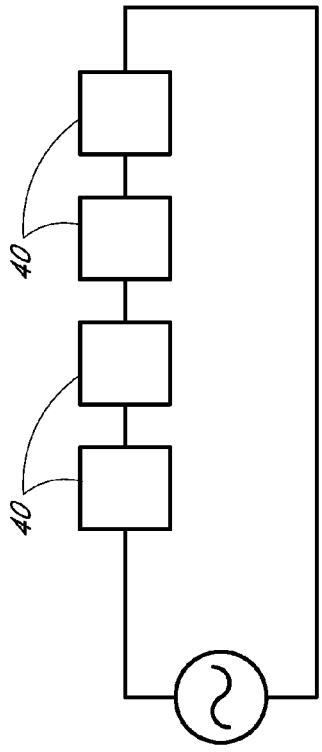
FIG. 8A illustrates a wiring diagram for connecting a plurality of ultrasound radiating members in parallel.
Figure 8B:
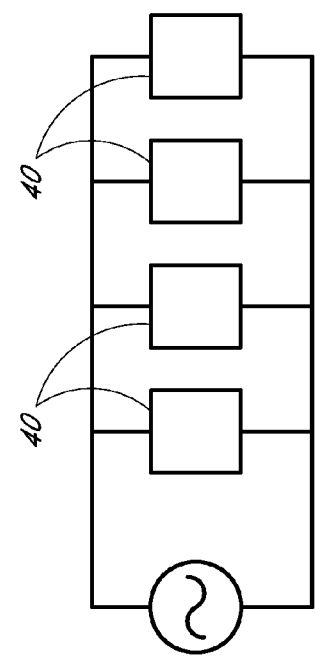
FIG. 8B illustrates a wiring diagram for connecting a plurality of ultrasound radiating members in series.

In embodiments wherein the catheter includes a plurality of ultrasound radiating members, ultrasound radiating member can be individually powered. For example, in one such embodiment, if the catheter includes n ultrasound radiating members, the catheter will also include 2n wires to individually power n ultrasound radiating members. In other embodiments, the ultrasound radiating members 40 can be electrically coupled in serial or in parallel, as illustrated in FIGS. 8A and 8B. These arrangements permit more flexibility as they use fewer wires. Each of the ultrasound radiating members can receive power simultaneously whether the ultrasound radiating members are in series or in parallel. When the ultrasound radiating members are connected in series, less current is required to produce the same power from each ultrasound radiating member than when the ultrasound radiating members are connected in parallel. The reduced current allows smaller wires to be used to provide power to the ultrasound radiating members, and accordingly increases the flexibility of the catheter. When the ultrasound radiating members are connected in parallel, an ultrasound radiating member can fracture or otherwise fail without breaking the current flow and interrupting the operation of the other ultrasound radiating members.

Figure 8C:
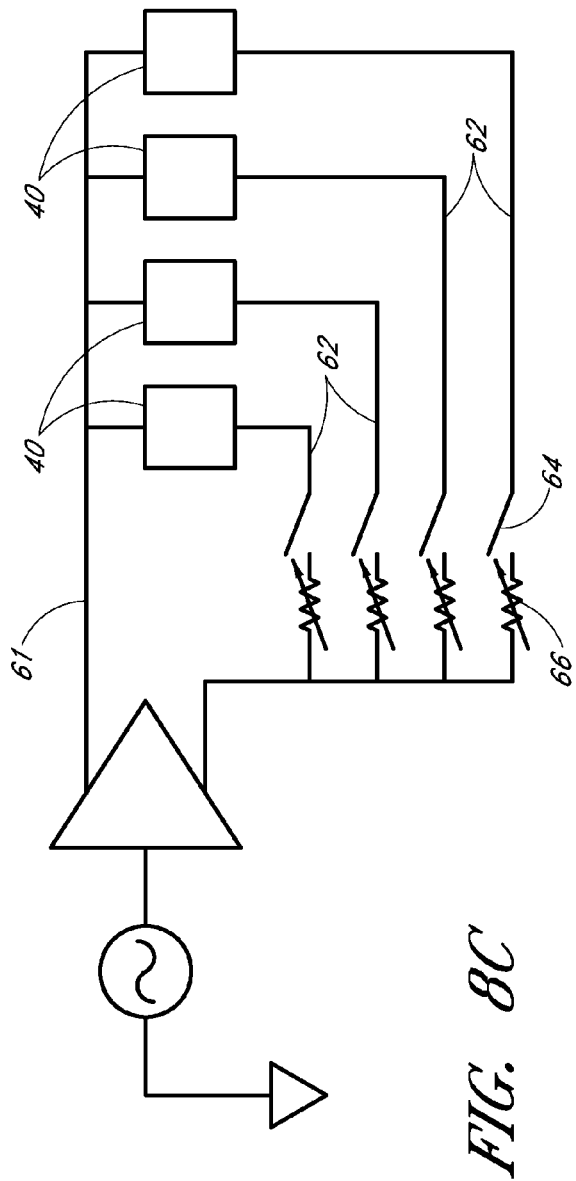
FIG. 8C illustrates a wiring diagram for connecting a plurality of ultrasound radiating members with a common wire.

In an exemplary embodiment, the output power of the ultrasound radiating members can be controlled. For example, as illustrated in FIG. 8C, a common wire 61 can provide power of plurality of ultrasound radiating members 40, while each ultrasound radiating member 40 has its own return wire 62. A particular ultrasound radiating member 40 can be individually activated by closing a switch 64 to complete a circuit between the common wire 61 and the return wire 62 associated with the particular ultrasound radiating member 40. Once a switch 64 corresponding to a particular ultrasound radiating member 40 has been closed, the amount of power supplied to the ultrasound radiating member 40 can be adjusted using a potentiometer 66. Accordingly, a catheter with n ultrasound radiating members 40 uses only n+1 wires, and still permits independent control of the ultrasound radiating members 40. This reduced number of wires increases the flexibility of the catheter. To further improve the flexibility of the catheter, the individual return wires 62 can have diameters which are smaller than the common wire 61 diameter. For instance, in an embodiment where n ultrasound radiating members are powered simultaneously, the diameter of the individual return wires 62 can be approximately the square root of n times smaller than the diameter of the common wire 61.

As illustrated in the exemplary embodiment illustrated in FIG. 3B, the catheter further includes one or more temperature sensors 20 located at the catheter distal end. (The small vessel catheter illustrated in FIG. 2B also optionally includes a temperature sensor 136.) In such embodiments, the inner core proximal end 36 includes a temperature sensor lead 24, which is operatively connected to the temperature sensors 20. In the modified embodiment illustrated in FIG. 3C, the temperature sensors 20 are positioned in the energy delivery section 18 on the surface of the outer sheath 16. In such embodiments, the temperature sensor lead 24 extends from the outer sheath proximal end. Suitable temperature sensors 20 include, but are not limited to, temperature sensing diodes, thermistors, thermocouples, RTDs, and fiber optic temperature sensors which use thermalchromic liquid crystals. Suitable temperature sensor 20 geometries include, but are not limited to, a point, patch, a stripe, and a band around the outer sheath 16. The temperature sensors 20 can be positioned on the outer sheath 16 or on the inner core 34 near the ultrasound radiating members 40. In an exemplary embodiment, the temperature sensors 20 are positioned near the energy delivery section 18.

Figure 9:
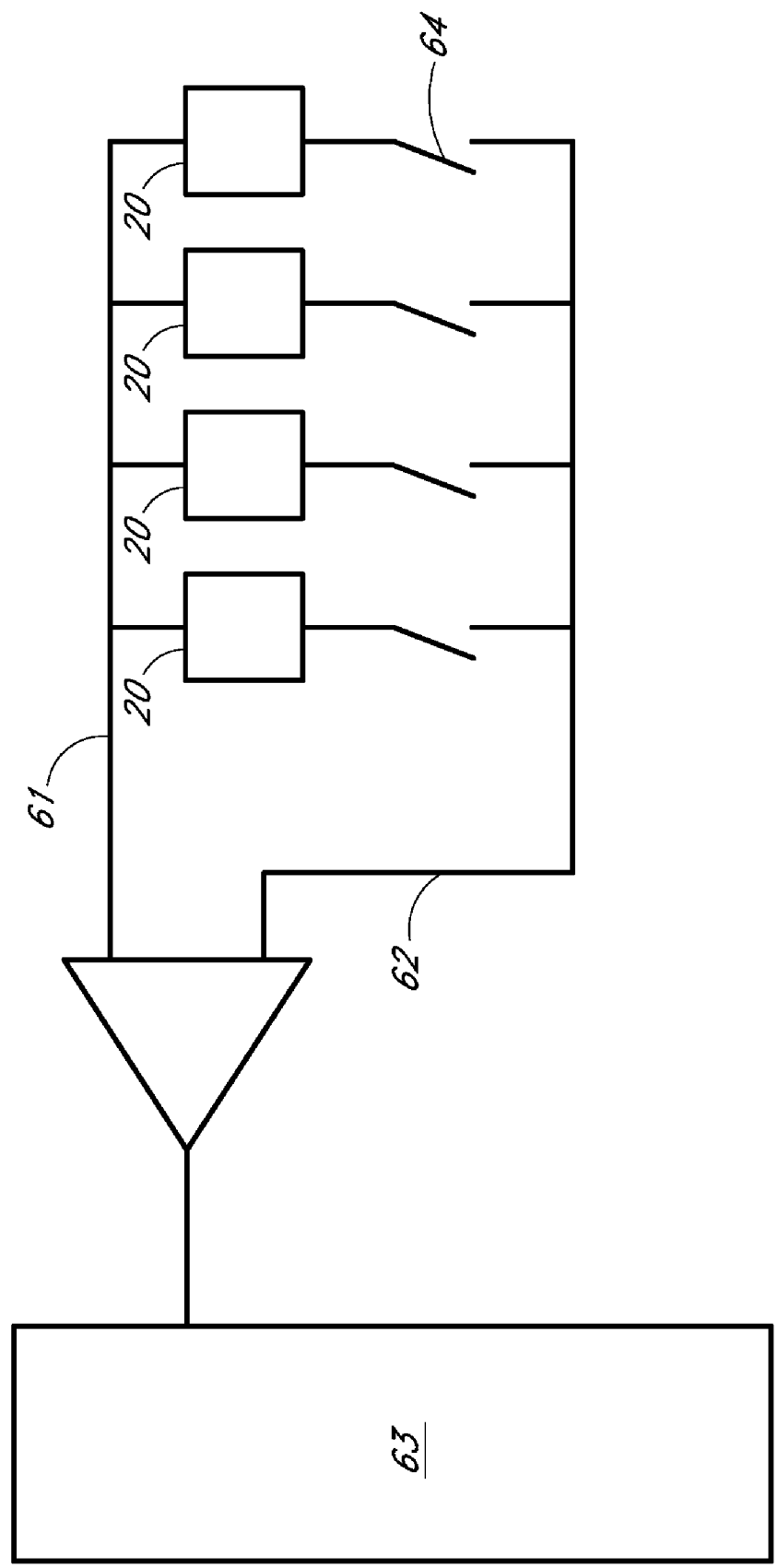
FIG. 9 a wiring diagram for connecting a plurality of temperature sensors with a common wire.

The temperature sensors 20 can be electrically connected as illustrated in FIG. 9. Each temperature sensor 20 can be coupled with a common wire 61 and an individual return wire 62. Accordingly, n+1 wires can be used to independently sense the temperature at n temperature sensors 20. The temperature at a particular temperature sensor 20 can be determined by closing a switch 64 to complete a circuit that includes the particular temperature sensor 20. When the temperature sensors 20 are thermocouples, the temperature can be calculated from the voltage in the circuit using, for example, a sensing circuit 63. To improve the flexibility of the outer sheath 16, the individual return wires 62 can have diameters which are smaller than the diameter of the common wire 61.

Each temperature sensor 20 can also be independently wired. In such embodiments, n independently wired temperature sensors 20 use 2n wires along the outer sheath 16.

The flexibility of the outer sheath 16 and inner core 34 can also be improved by using fiber optic based temperature sensors 20. Particularly, in such embodiments only n fiber optics are used to sense the temperature at n temperature sensors 20.

Figure 10:
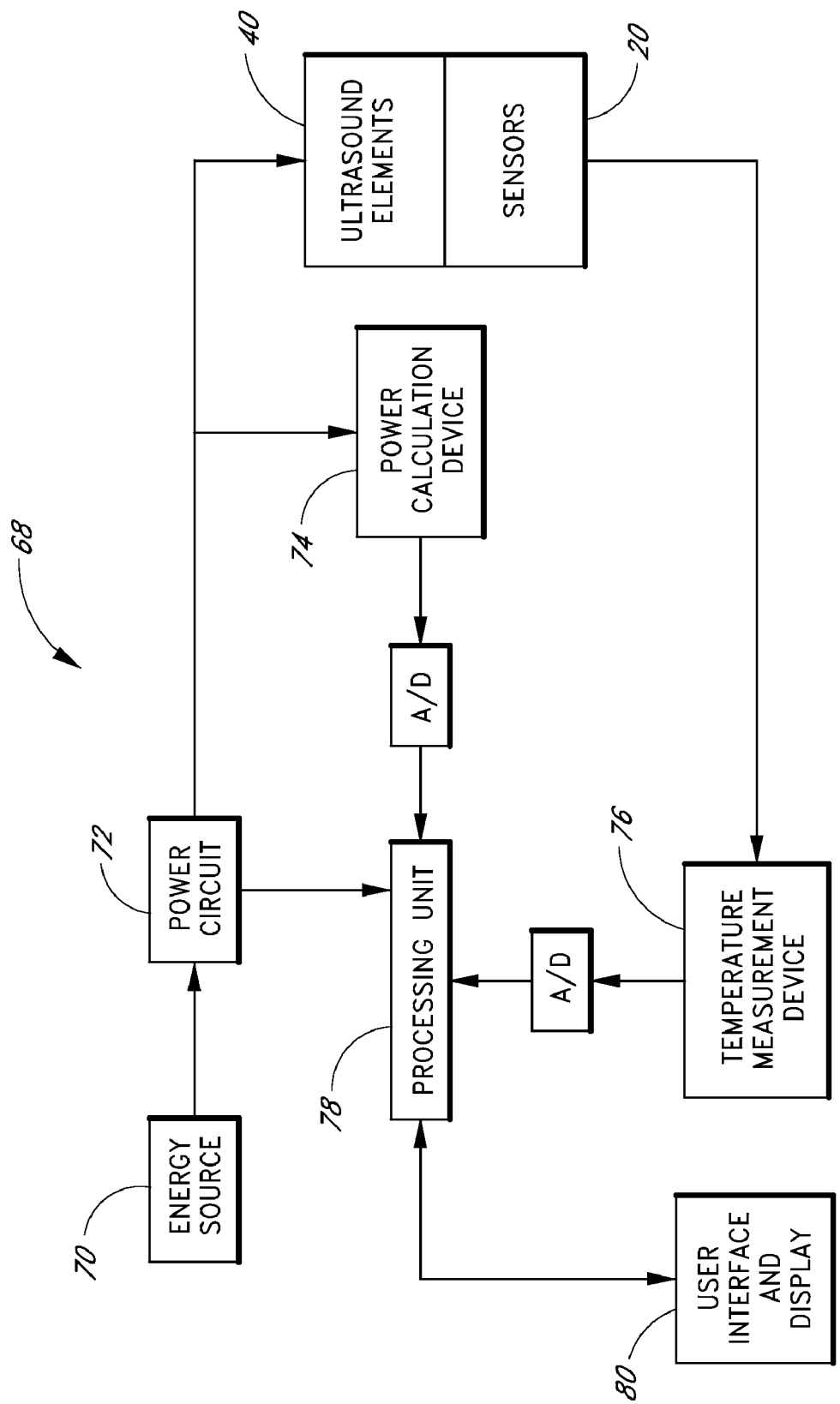
FIG. 10 is a block diagram of a feedback control system for use with an ultrasonic catheter

The catheter 10 can be used with a feedback control system 68, as illustrated in FIG. 10. In such embodiments, the temperature at each temperature sensor 20 is monitored, and the output power of the energy source 70 is adjusted accordingly. The physician can, if desired, override the closed or open loop system.

In the exemplary embodiment illustrated in FIG. 10, the feedback control system 68 includes an energy source 70, a power circuit 72, and a power calculation device 74 coupled with the ultrasound radiating members 40. A temperature measurement device 76 is coupled with the temperature sensors 20 on the outer sheath 16 or the inner core 34. A processing unit 78 is coupled with the power calculation device 74, the power circuits 72, and a user interface and display 80.

In operation, the temperature at the temperature sensors 20 is determined at the temperature measurement device 76. The processing unit 78 receives the determined temperatures from the temperature measurement device 76. The determined temperatures can then be displayed to the user at the user interface and display 80.

The processing unit 78 includes logic for generating a temperature control signal. The temperature control signal is proportional to the difference between the measured temperature and a desired temperature. The desired temperature can be determined by the user or be preset within the processing unit 78. For example, in an exemplary embodiment, the user sets the desired temperature using the user interface and display 80.

The temperature control signal is received by the power circuit 72. The power circuit 72 can be configured to adjust the power level, voltage, phase and/or current of the energy supplied to the ultrasound radiating members 40 from the energy source 70. For instance, when the temperature control signal is above a particular level, the power supplied to a particular ultrasound radiating member 40 can be reduced in response to the temperature control signal. Similarly, when the temperature control signal is below a particular level, the power supplied to a particular ultrasound radiating member 40 can be increased in response to the magnitude of the temperature control signal. After each power adjustment, the processing unit 78 monitors the temperature sensors 20 and produces another temperature control signal which is received by the power circuits 72.

The processing unit 78 can also include safety control logic. The safety control logic detects when the temperature at a temperature sensor 20 has exceeded a safety threshold. The processing unit 78 can then provide a temperature control signal which causes the power circuit 72 to reduce or stop the delivery of energy from the energy source 70 to the ultrasound radiating members 40.

Because the ultrasound radiating members 40 can move relative to the temperature sensors 20 in certain embodiments, it can be unclear which ultrasound radiating member should have a power, voltage, phase and/or current level adjustment. Consequently, each ultrasound radiating member 40 is identically adjusted in one embodiment. In a modified arrangement, the power, voltage, phase, and/or current supplied to each of the ultrasound radiating members 40 is adjusted in response to the temperature sensor 20 which indicates the highest temperature. Making voltage, phase and/or current adjustments in response to the temperature of the temperature sensor 20 indicating the highest temperature can reduce the likelihood that the treatment site overheats.

The processing unit 78 can be configured to receive a power signal from the power calculation device 74. The power signal can be used to determine the power being received by each ultrasound radiating member 40. The determined power can then be displayed to the user on the user interface and display 80.

The feedback control system 68 can maintain the treatment site within a desired temperature range. For example, to prevent the temperature of the treatment site from increasing more than 6° C. above body temperature, and thus causing tissue damage, the ultrasound radiating members 40 can be independently monitored and controlled as described above. In one embodiment, the processing unit 78 can be preprogrammed to drive each ultrasound radiating member 40 at a predetermined energy for a predetermined length of time.

The processing unit 78 can comprise a digital or analog controller, or a computer with software. In embodiments wherein the processing unit 78 is a computer, it can include a central processing unit coupled through a system bus. The user interface and display 80 can comprise a mouse, keyboard, a disk drive or other non-volatile memory system, a display monitor, and other peripherals. Program memory and data memory can also be coupled to the bus.

In lieu of the series of power adjustments described above, a profile of the power to be delivered to each ultrasound radiating member 40 can be incorporated in the processing unit 78. A preset amount of energy to be delivered can also be profiled. The power delivered to each ultrasound radiating member 40 can the be adjusted according to the profiles.

Methods of Use

Figure 11A:
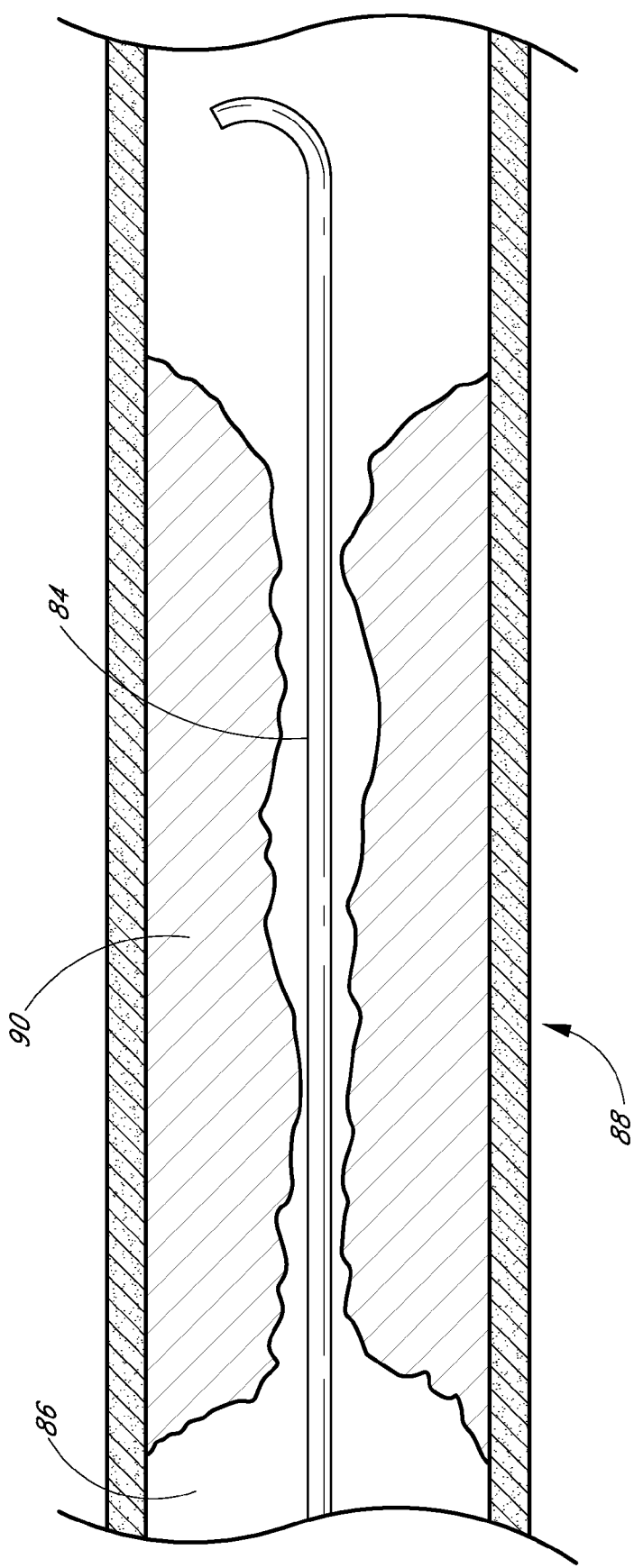
FIG. 11A is a cross-sectional view of a treatment site.

FIGS. 11A through 11G illustrate an exemplary method for using the ultrasonic catheter 10. This method is applicable to both long segment and small vessel catheters. In FIG. 11A, a guidewire 84 similar to a guidewire used in typical angioplasty procedures is directed through vessels 86 toward a treatment site 88 which includes a clot 90. The guidewire 84 is optionally directed through the clot 90. Suitable vessels include, but are not limited to, the large periphery blood vessels of the body. Of course, as mentioned above, the ultrasonic catheter 10 can also be used for various imaging applications and for treating and/or diagnosing other diseases in other body parts.

Figure 11B:
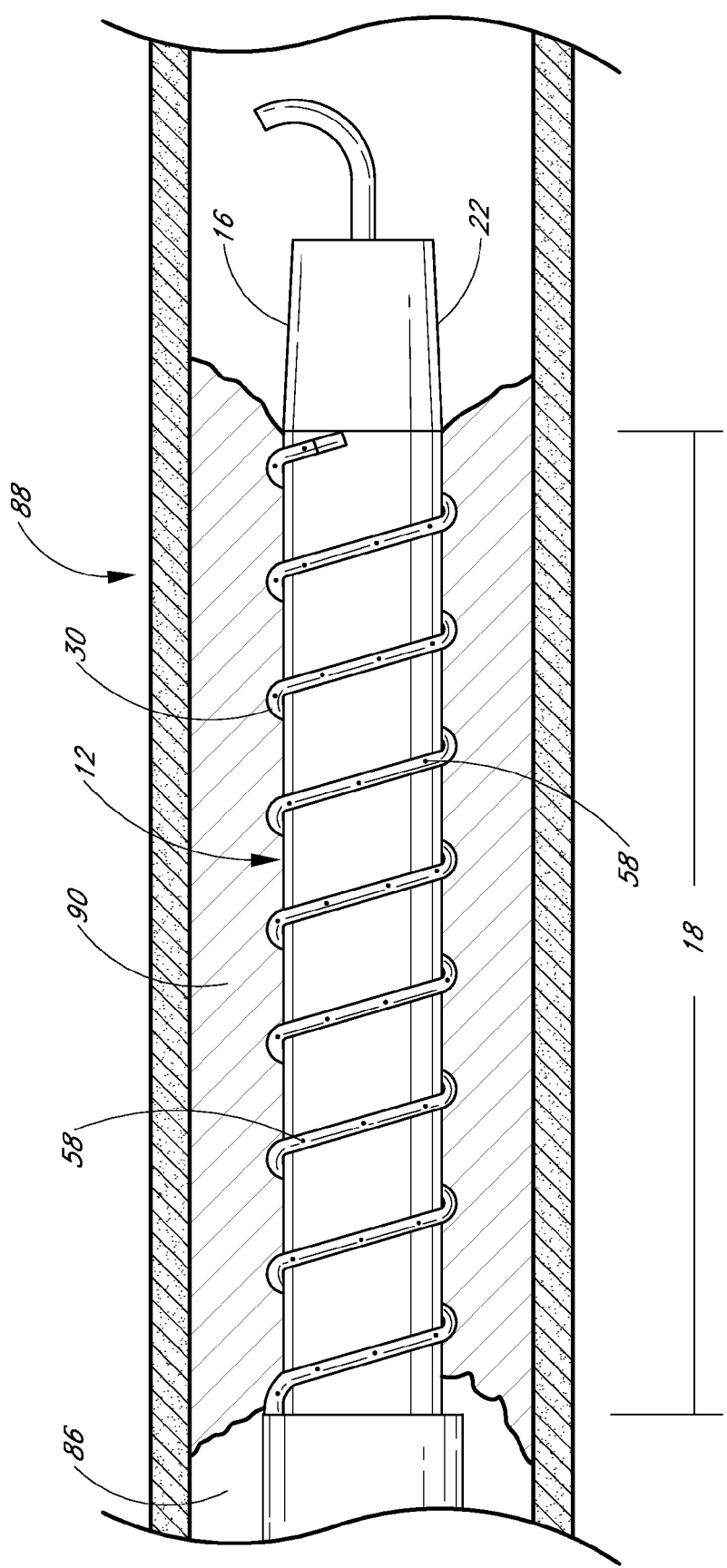
FIG. 11B is a side view of the distal end of an ultrasonic catheter positioned at the treatment site.

In FIG. 11B, the outer sheath 16 is advanced over the guidewire 84 using over-the-guidewire techniques. The outer sheath 16 is advanced until the energy delivery section 18 is positioned at the clot 90. Radiopaque markers are optionally positioned at the energy delivery section 18 of the outer sheath 16 to aid in the positioning of the outer sheath 16 within the treatment site 88.

Figure 11C:
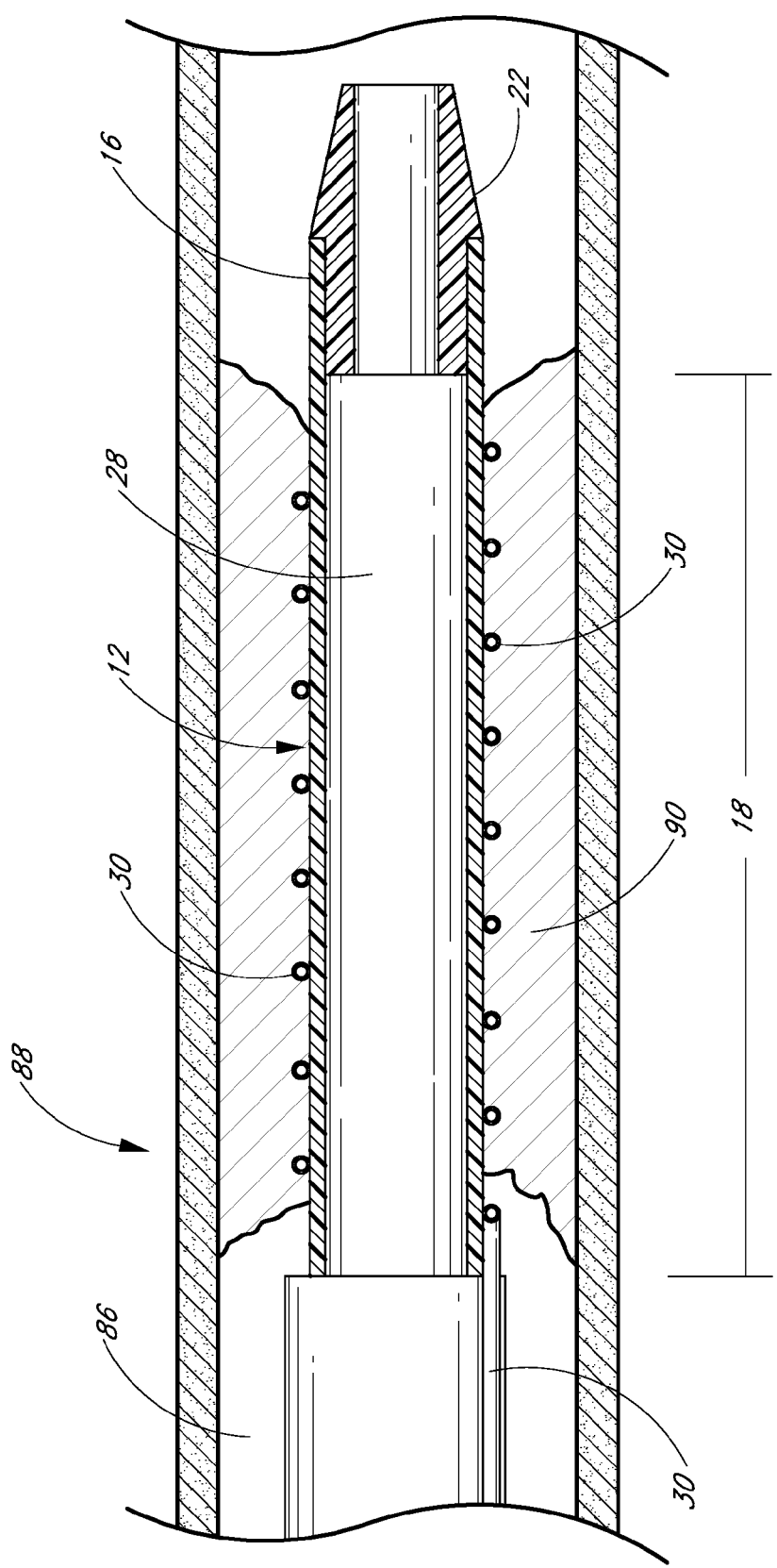
FIG. 11C is a cross-sectional view of the distal end of the ultrasonic catheter of FIG. 11B positioned at the treatment site.

Referring now to FIG. 11C, the guidewire 84 is withdrawn from the utility lumen 28 by pulling the guidewire 84 proximally while holding the outer sheath 16 stationary.

Figure 11D:
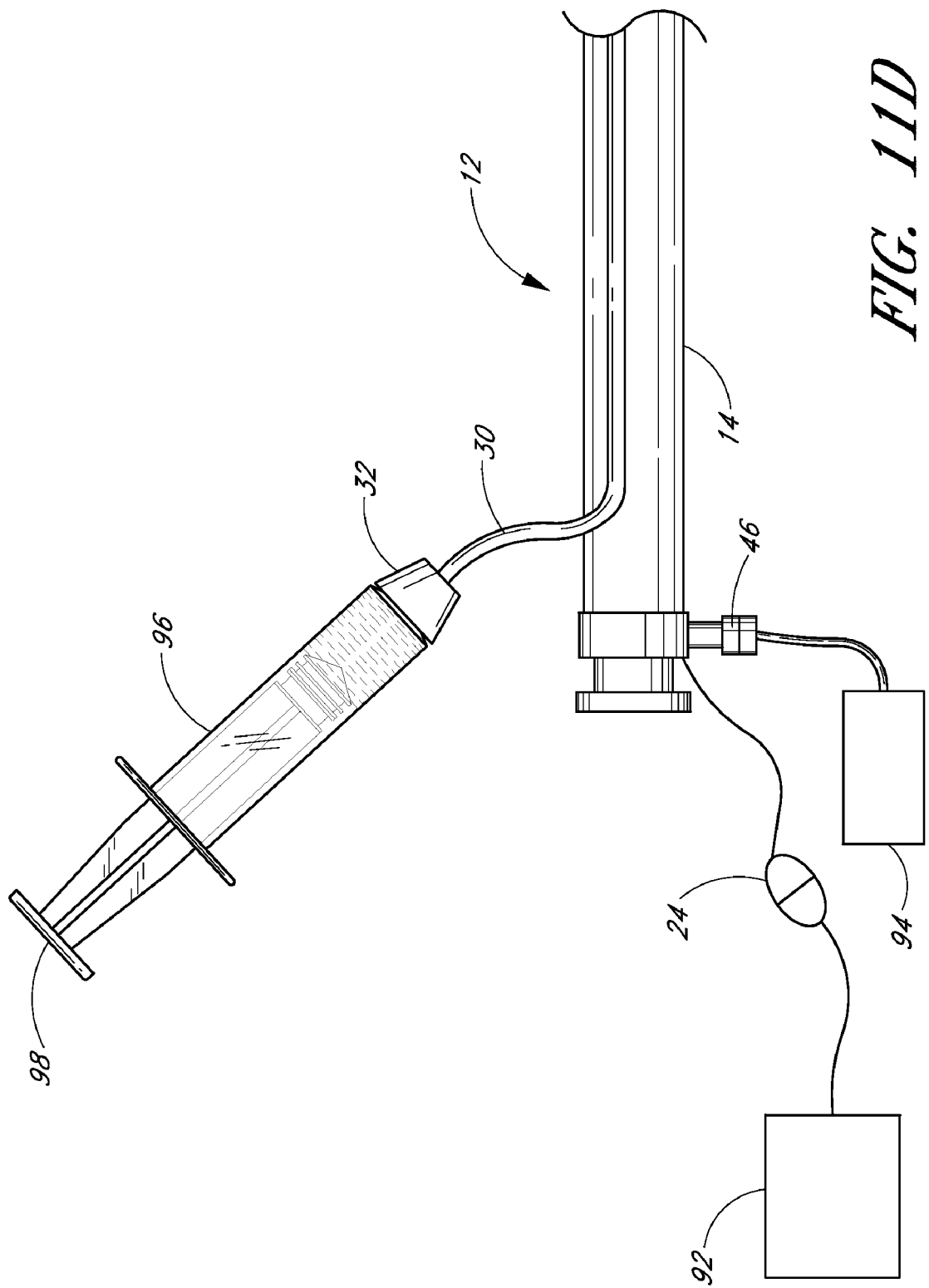
FIG. 11D is a side view of the proximal end of the ultrasonic catheter of FIG. 11B.
Figure 11E:
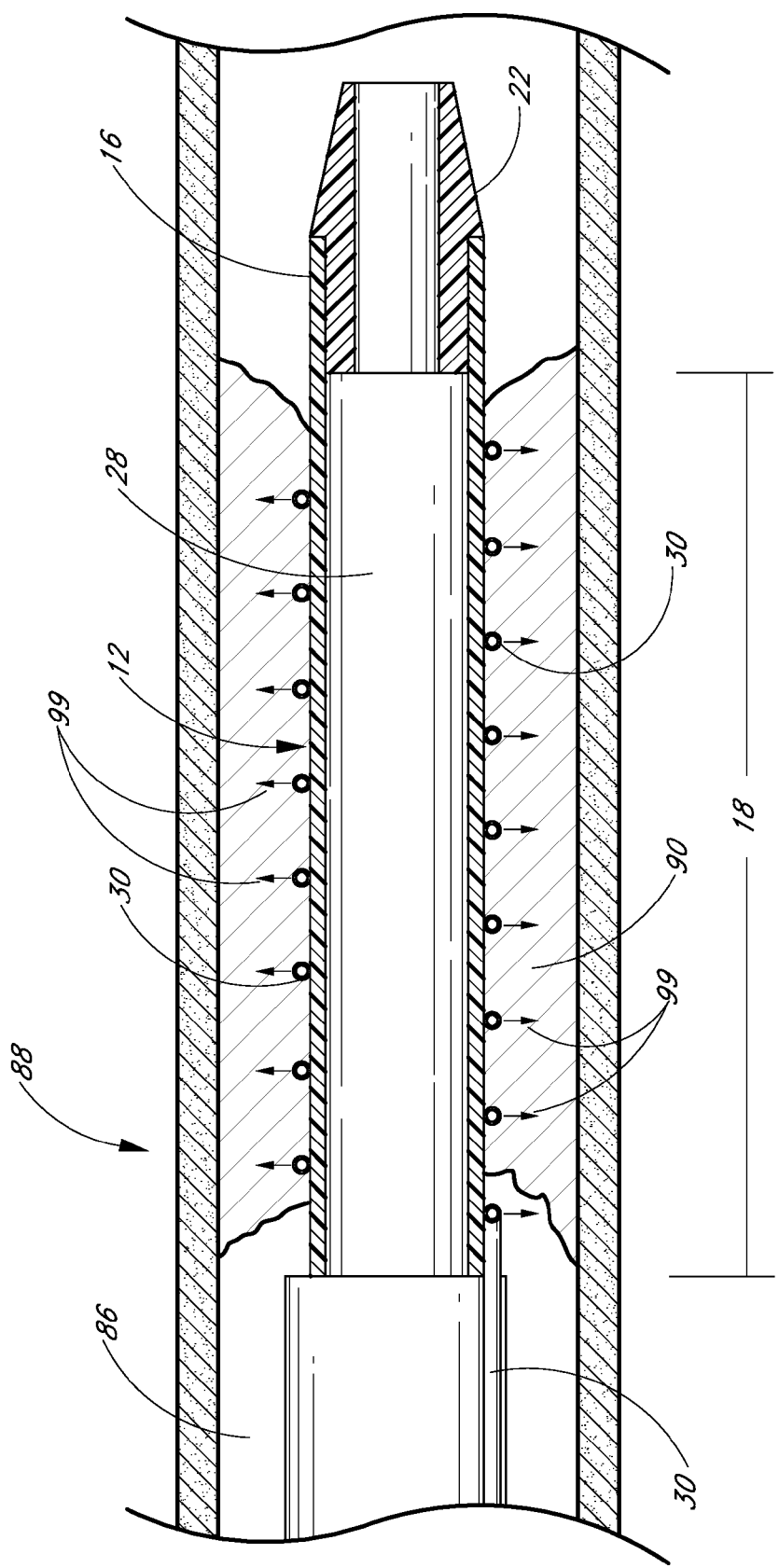
FIG. 11E is a cross-sectional view of the distal end of the ultrasonic catheter of FIG. 11B positioned at the treatment site.

In FIG. 11D, a temperature monitor 92 is coupled with the temperature sensor leads 24, a cooling fluid source 94 is coupled with the cooling fluid fitting 46, and a therapeutic compound solution source 96 is coupled with the inlet port 32. The therapeutic compound solution source 96 can be a syringe with a Luer fitting that is complementary to the inlet port 32. Pressure can be applied to a plunger 98 on the therapeutic compound solution source 96, thereby driving the therapeutic compound through the delivery lumen 30. The therapeutic compound is delivered from the delivery lumen 30 through the delivery ports 58 as illustrated by the arrows 99 in FIG. 11E. Suitable therapeutic compounds include, but are not limited to, an aqueous solution containing a thrombolytic agent (that is, a clot-dissolving drug), such as, heparin, urokinase, streptokinase, TPA and BB-10153. In other embodiments, wherein the ultrasonic catheter is not used to remove a thrombus, other therapeutic compounds (such as cancer treating drugs, genetic material, light activated drugs and so forth) can be delivered through the delivery lumen.

Figure 11F:
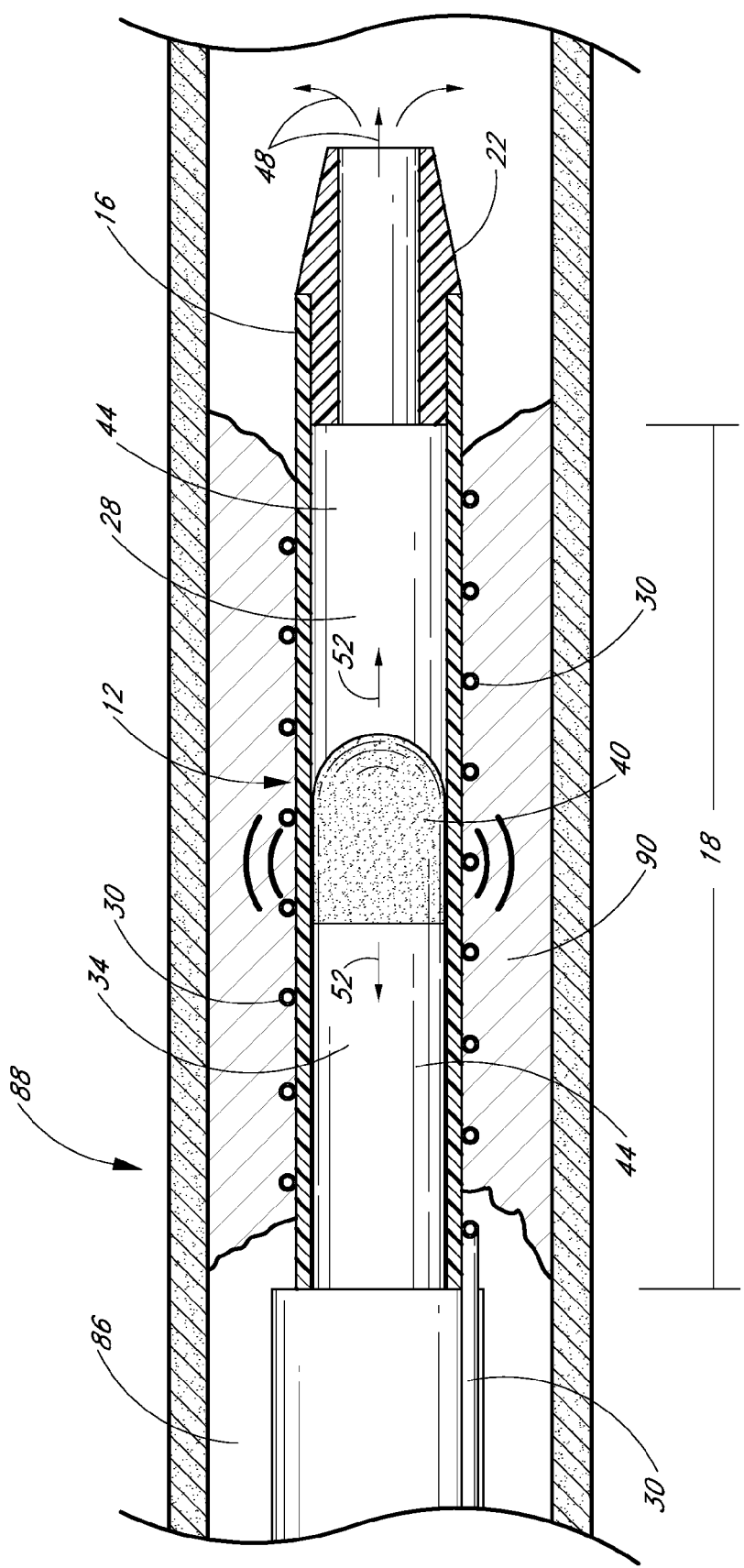
FIG. 11F is a cross-sectional view of the distal end of the ultrasonic catheter of FIG. 11B positioned at the treatment site showing the movement of the inner core.

Referring now to FIG. 11F, in embodiments wherein the ultrasound radiating member 40 is movable with respect to the utility lumen 28, the inner core 34 is inserted into the utility lumen 28 until the ultrasound radiating member 40 is positioned within the energy delivery section 18. To aid in positioning the ultrasound radiating member 40, radiopaque markers can be affixed to the inner core 34 adjacent the ultrasound radiating members 40, or the ultrasound radiating members 40 themselves can be radiopaque. In a modified embodiment, the ultrasonic energy radiated by the ultrasound radiating members 40 can be used to aid placement. Once the inner core 34 is properly positioned, the ultrasound radiating member 40 is activated to deliver ultrasonic energy through the energy delivery section 18 to the clot 90. In one embodiment, the ultrasonic energy has a frequency between approximately 20 kHz and approximately 20 MHz. In another embodiment, the frequency is between about 500 kHz and about 20 MHz. In another embodiment, the frequency is between about 1 MHz and about 3 MHz. In another embodiment, the frequency is about 3 MHz. While the ultrasonic energy is being delivered, the ultrasound radiating member 40 can optionally be moved within the energy delivery section 18 as illustrated by the arrows 52. The ultrasound radiating member 40 can be moved within the energy delivery section 18 by manipulating the inner core proximal end 36 while holding the backend hub 33 stationary. In the illustrated embodiment, a cooling fluid flows through the cooling fluid lumen 44 and out the occlusion device 22.

Figure 11G:
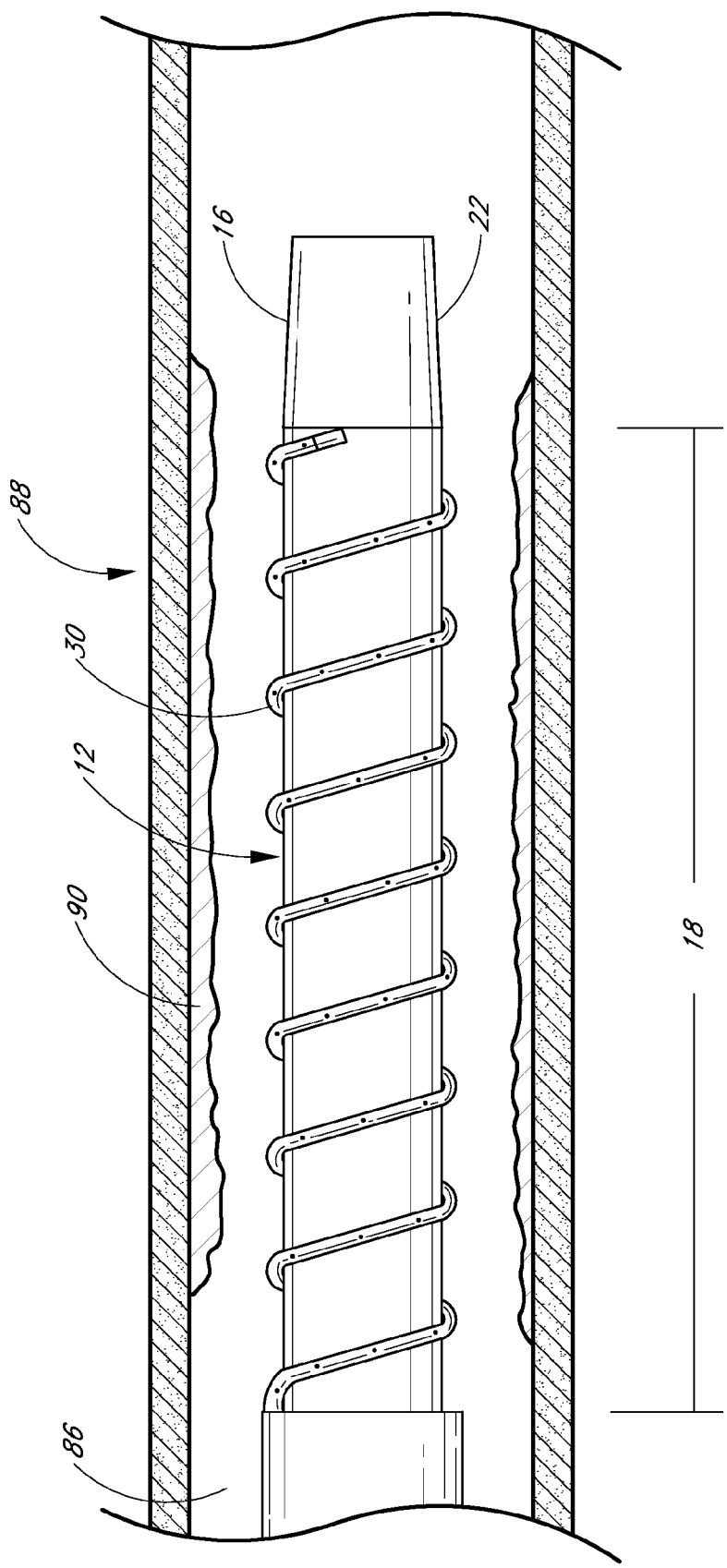
FIG. 11G is a side view of the distal end of the ultrasonic catheter of FIG. 11B positioned at the treatment site.

The cooling fluid can be delivered before, after, during or intermittently with the delivery of the ultrasonic energy. Similarly, the therapeutic compound can be delivered before, after, during or intermittently with the delivery of ultrasonic energy. As a result, the acts illustrated in FIGS. 11A through 11F can be performed in different orders than are described above. The therapeutic compound and energy are applied until the clot 90 is partially or entirely dissolved, as illustrated in FIG. 11G. Once the clot 90 has been sufficiently dissolved, the outer sheath 16 and inner core 34 are withdrawn from the treatment site 88.

Further information regarding other techniques for treating a clot using ultrasonic energy delivered from a catheter can be found in Applicant's co-pending U.S. patent application Ser. No. 09/107,078, which is hereby incorporated herein by reference in its entirety.

Ultrasound Radiating Members

Structures

A wide variety of ultrasound radiating member configurations can be used with the catheters described above. As evident from the foregoing description, in certain embodiments the ultrasound radiating members comprise an elongate cylinder of piezoelectric material having a hollow core through which materials such as a cooling fluid, a therapeutic compound, or electrical conductors can be passed. Such ultrasound radiating member embodiments can be used with both long segment and small vessel ultrasonic catheters.

Figure 12A:
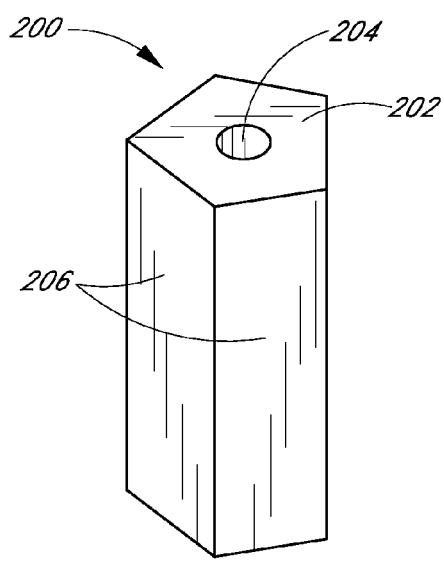
FIG. 12A is a perspective view of an ultrasound radiating member having pentagonal front and rear faces.
Figure 12B:
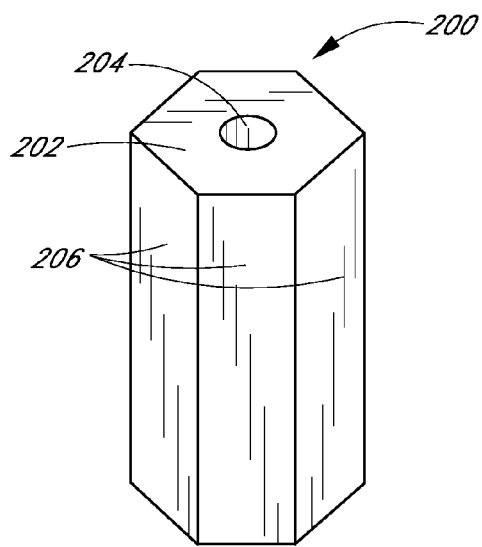
FIG. 12B is a perspective view of an ultrasound radiating member having hexagonal front and rear faces.
Figure 12C:
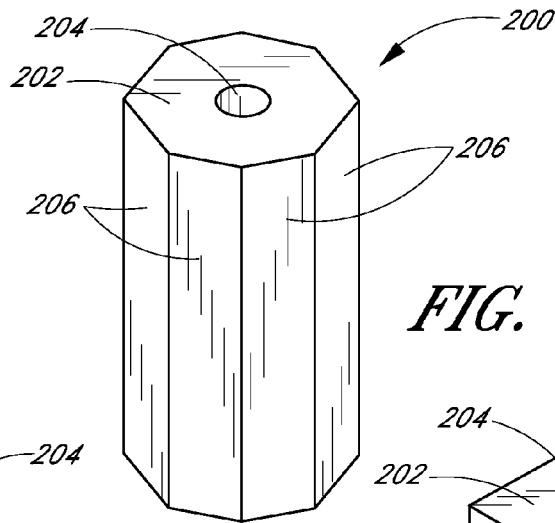
FIG. 12C is a perspective view of an ultrasound radiating member having octagonal front and rear faces.
Figure 12D:
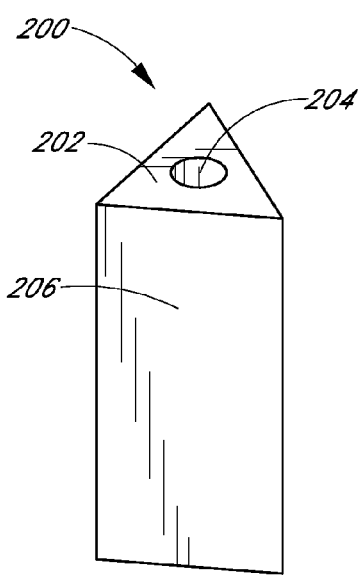
FIG. 12D is a perspective view of an ultrasound radiating member having triangular front and rear faces.
Figure 12E:
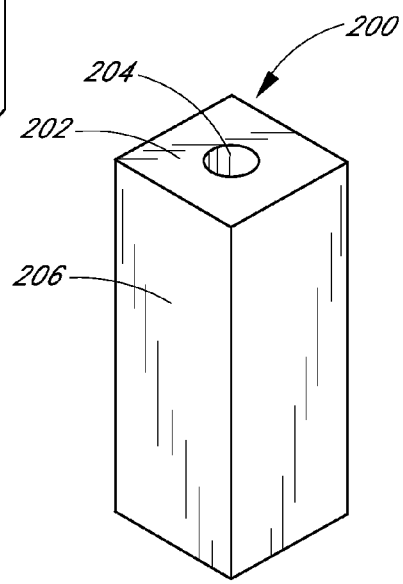
FIG. 12E is a perspective view of an ultrasound radiating member having rectangular front and rear faces.
Figure 13:
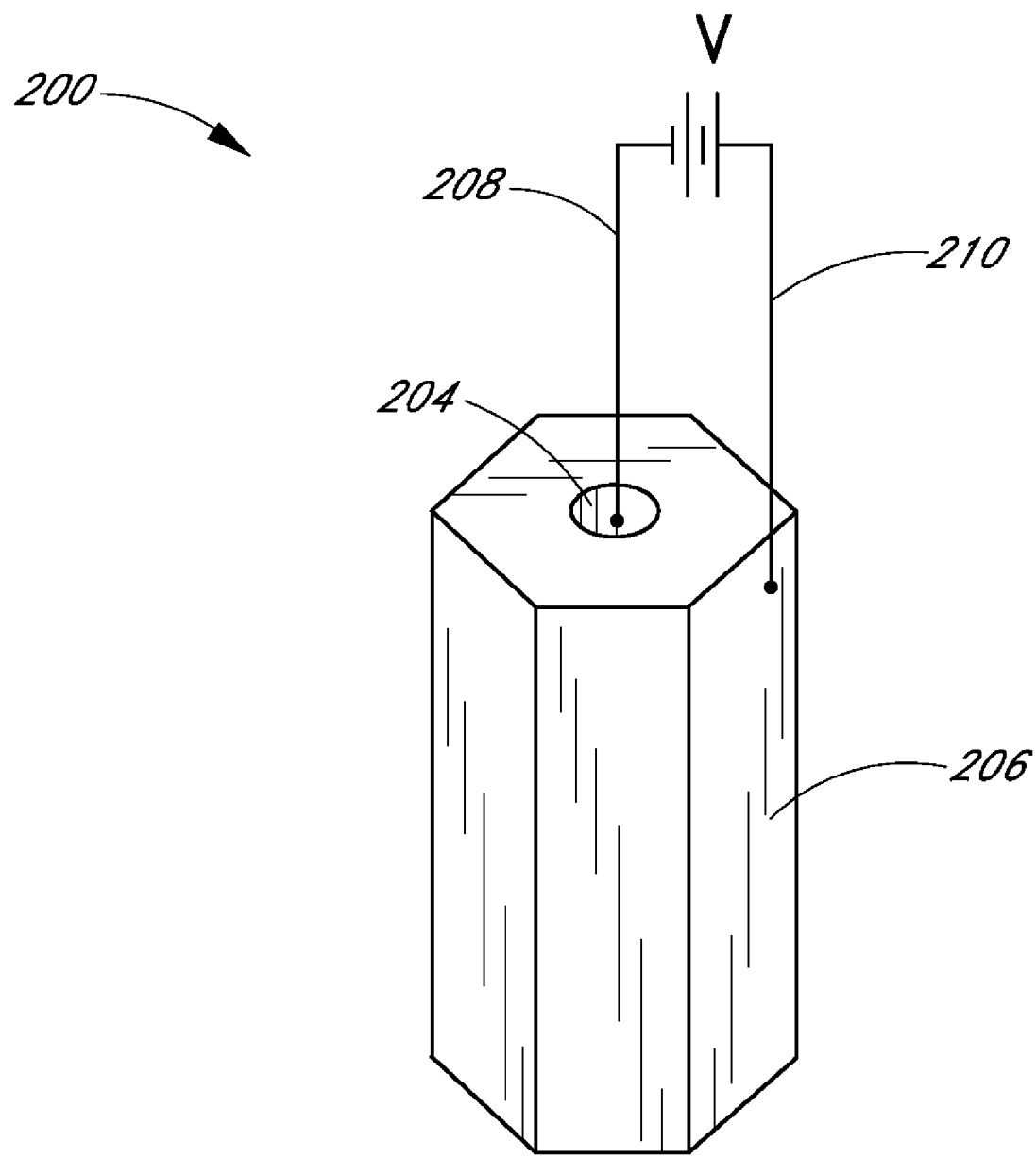
FIG. 13 is a perspective view of an ultrasound radiating member having first and second wires connected to inner and outer surfaces, respectively.

Exemplary embodiments of an ultrasound radiating member 200 are illustrated in FIGS. 12A through 12E. In these embodiments, the ultrasound radiating member 200 comprises a front face 202, a rear face (not shown) that is opposite the front face, and a hollow central core 204 that extends along the longitudinal axis of the ultrasound radiating member 200. In such embodiments, the front and rear faces form an n-sided polygon. For example, in FIG. 12A, the front and rear faces have five sides and form a pentagon. In FIG. 12B, the front and rear faces have six sides and form a hexagon. In FIG. 12C, the front and rear faces have eight sides and form an octagon. In FIG. 12D, the front and rear faces have three sides and form a triangle. In FIG. 12E, the front and rear faces have four sides and form a square. In these embodiments, the sides of the front and rear faces are connected by generally rectangular side faces 206, which together form the outer surface of the ultrasound radiating member 200.

As described herein, in an exemplary embodiment the ultrasound radiating member 200 comprises a piezoelectric ceramic or a similar material. In one embodiment, illustrated in FIG. 13, the side faces 206 and the central core 204 are coated with a conductive material. The conductive material can be applied using an appropriate application technique, such as electroplating. A first wire 208 is attached to the central core 204, and a second wire 210 is connected to at least one of the side faces 206. In such embodiments, application of a voltage difference 212 across the first and second wires causes the ultrasound radiating member 200 to generate ultrasonic energy.

In a modified embodiment, the ultrasound radiating member 200 is mounted directly on an elongate member that extends through the central core 204. This configuration is particularly advantageous in applications where a plurality of ultrasound radiating members are to be mounted within the inner core 34, as disclosed herein and as illustrated in FIGS. 3B and 4A. The ultrasound radiating members can be electrically connected in series or in parallel. For example, in an embodiment wherein the ultrasound radiating members are electrically connected in parallel, a common wire runs through, and is electrically connected to, the centers of several ultrasound radiating members, and a second wire runs along, and is electrically connected to, the side faces of the ultrasound radiating members. In an embodiment wherein the ultrasound radiating members are electrically connected in series, an electrically insulating core runs through the centers of several ultrasound radiating members, and a wire connects the inner electrode and the outer electrode of adjacent ultrasound radiating members. In still other embodiments, the ultrasound radiating members can be electrically grouped, such that a separate groups of ultrasound radiating members can be individually activated.

The embodiments disclosed herein advantageously allow a plurality of ultrasound radiating members to be mounted within an inner core 34 that is configured to be inserted into the tubular body of an ultrasonic catheter. The ultrasound radiating members illustrated in FIGS. 12A through 12E are particularly well suited for such applications, because structural members, electrical members, and/or fluids can be passed through the central core 204.

The ultrasound radiating members 200 illustrated in FIGS. 12A through 12E have several advantages. For example, such ultrasound radiating members 200 have more radiating faces and thus produce a more radially uniform distribution of ultrasound energy as compared to a rectangular block or flat plate. Moreover, as compared to cylindrical ultrasound members, the ultrasound radiating members 200 described herein have a larger output region and have lower mechanical stresses during operation. Lower mechanical stresses during operation result in lower failure rates.

Although not illustrated, modified embodiments of the ultrasound radiating members 200 have side faces 206 that are non-rectangular (for example, square or tapered) and/or not identical.

Ultrasound Radiating Members

Manufacturing Techniques

Improved methods for manufacturing ultrasound radiating members, including the ultrasound radiating members illustrated in FIGS. 12A through 12E are described herein.

Figure 14:
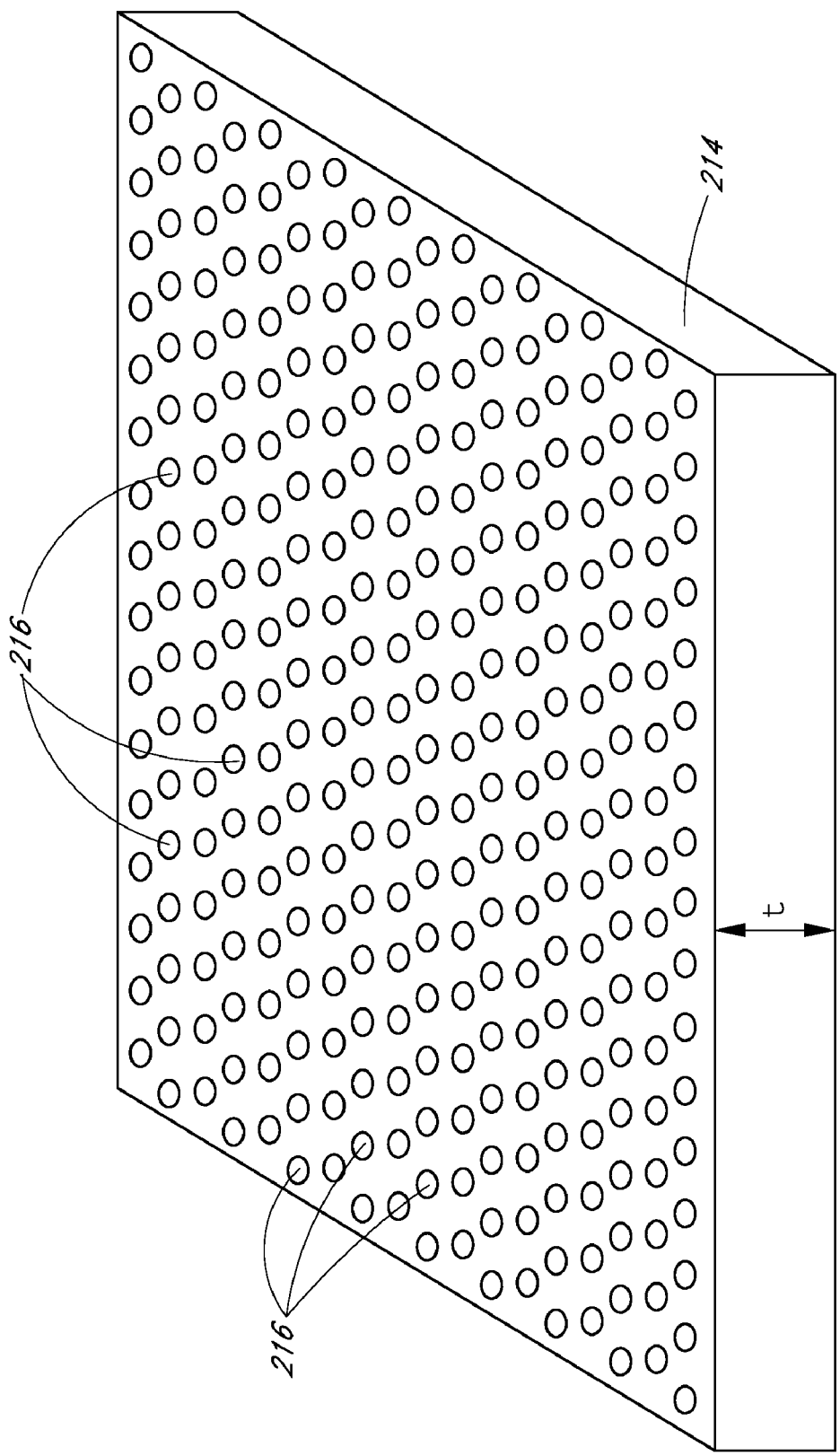
FIG. 14 is a perspective view of a sheet of piezoelectric material perforated with through or blind holes.

As illustrated in FIG. 14, a sheet 214 of piezoelectric ceramic or similar material is provided. In an exemplary embodiment, the sheet 214 has a thickness t that is greater than the length of the finished ultrasound radiating member. A plurality of holes 216 are then drilled into the sheet 214. In an exemplary embodiment, the holes 216 are drilled in a uniform pattern. In one embodiment, the holes 216 are through holes, which extend through the sheet 214. In another embodiment, the holes 216 are blind holes that do not extend through the sheet 214. In exemplary embodiments wherein the holes 216 are blind hoes, the blind holes are drilled to a depth that is greater than the length of the finished ultrasound radiating member.

Figure 15A:
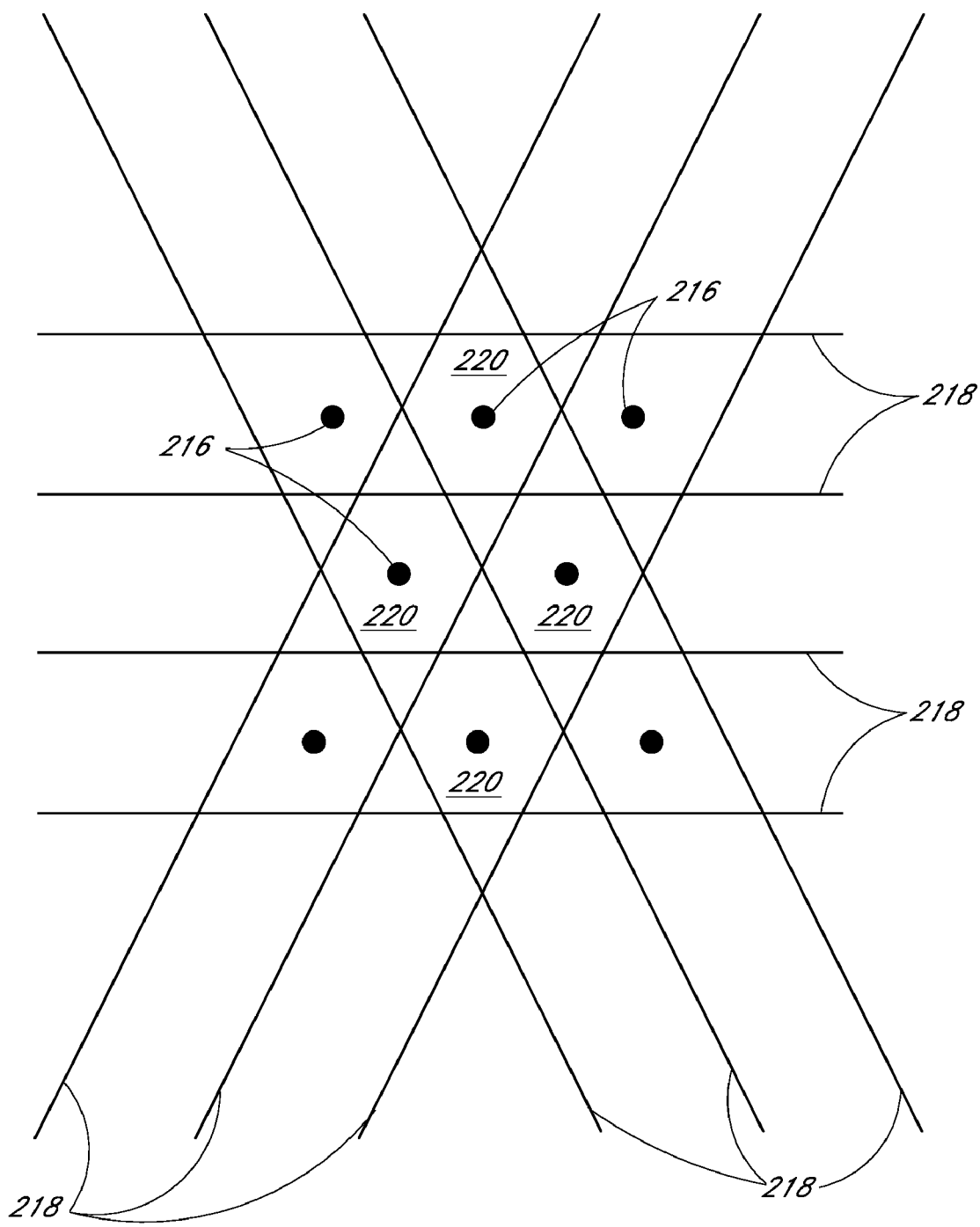
FIG. 15A is a plan view of the piezoelectric sheet of FIG. 14 having been cut to produce ultrasound radiating members having a hexagonal geometry.
Figure 15B:
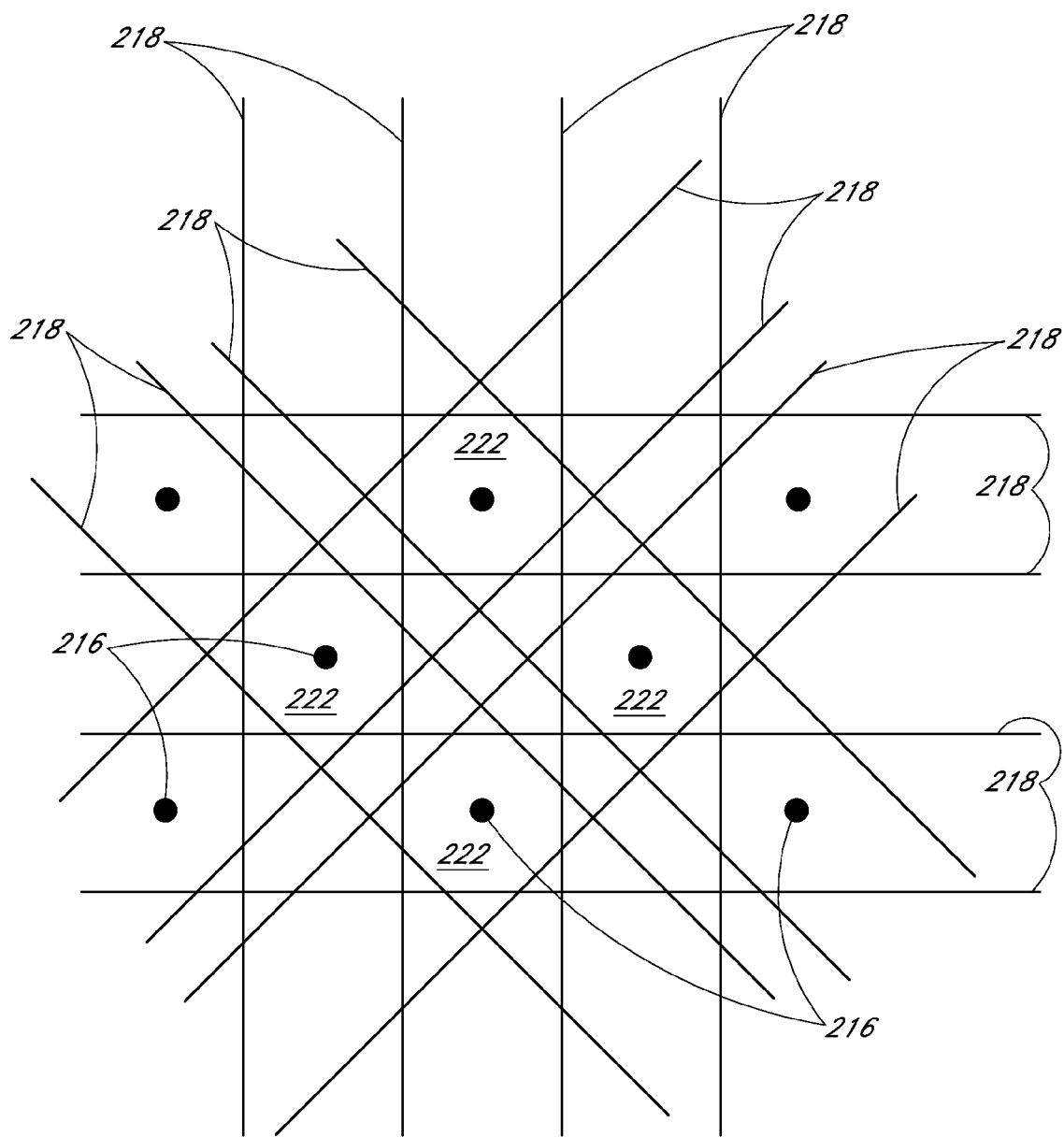
FIG. 15B is a plan view of the piezoelectric sheet of FIG. 14 having been cut to produce ultrasound radiating members having a octagonal geometry.

Referring now to FIGS. 15A and 15B, in an exemplary embodiment, the perforated sheet 214 is then diced with a dicing blade or other precision cutting tool to produce an n-sided polygonal geometry. For example, in FIG. 15A, a pattern of cuts 218 are used to produce a hexagonal ultrasound radiating member 220 centered about each hole 216. In FIG. 15B, the pattern of cuts 218 produces an octagonal ultrasound radiating member 222 that is centered about each hole 216. In other embodiments, the cuts 218 can be arranged to form other polygons with more or fewer sides, such as, triangles, squares, and pentagons. The triangular geometry, illustrated in FIG. 12D, is particularly advantageous because it requires a minimum number of cuts while producing no wasted piezoelectric material.

Figure 16:
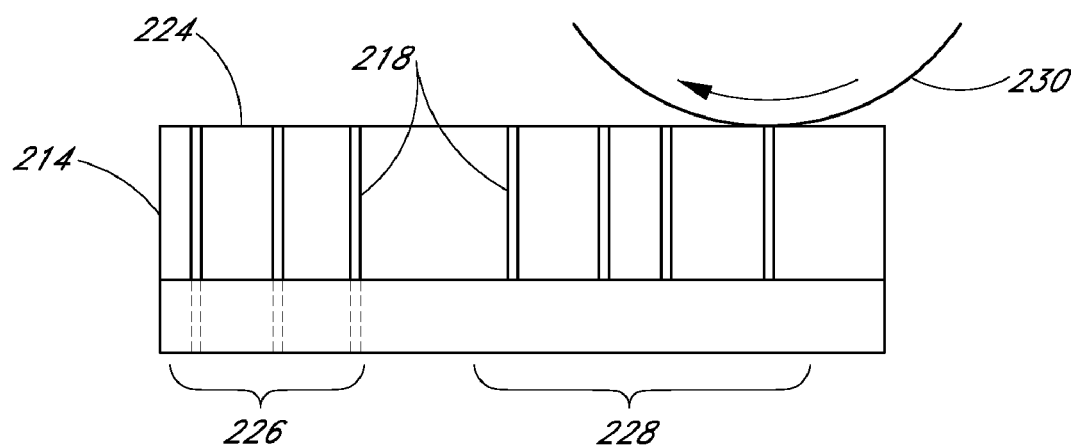
FIG. 16 is a cross-sectional view of the cut piezoelectric sheet of FIG. 15A or 15B.

In an exemplary embodiment, the cuts 218 do not extend through the piezoelectric sheet 214. However, in other embodiments, the cuts 218 do extend through the piezoelectric sheet 214. For example, as illustrated in FIG. 16, in a first region 226, the cuts 218 extend through the piezoelectric sheet 214; in a second region 228, the cuts 218 do not extend through the piezoelectric sheet 214. In embodiments wherein the cuts 218 do not extend through the piezoelectric sheet 214, the holes 216 (illustrated in FIG. 14) can be drilled deeper than the cuts 218.

Still referring to FIG. 16, after the cuts 218 are made, the upper surface of the sheet, which includes the interior surfaces of the holes 216 and the interior surfaces of the cuts 218, are plated with a conductive coating. This plating process provides a conductive coating on the central core 204 and the side faces 206 of the ultrasound radiating members to be harvested from the piezoelectric sheet. In such embodiments, plating material deposited on the top surface 224 of the sheet (that is, on the front or rear faces of the ultrasound radiating members 200) can be removed using a grinding wheel 230, by milling, or using other methods (for example, by grit blasting).

Figure 17:
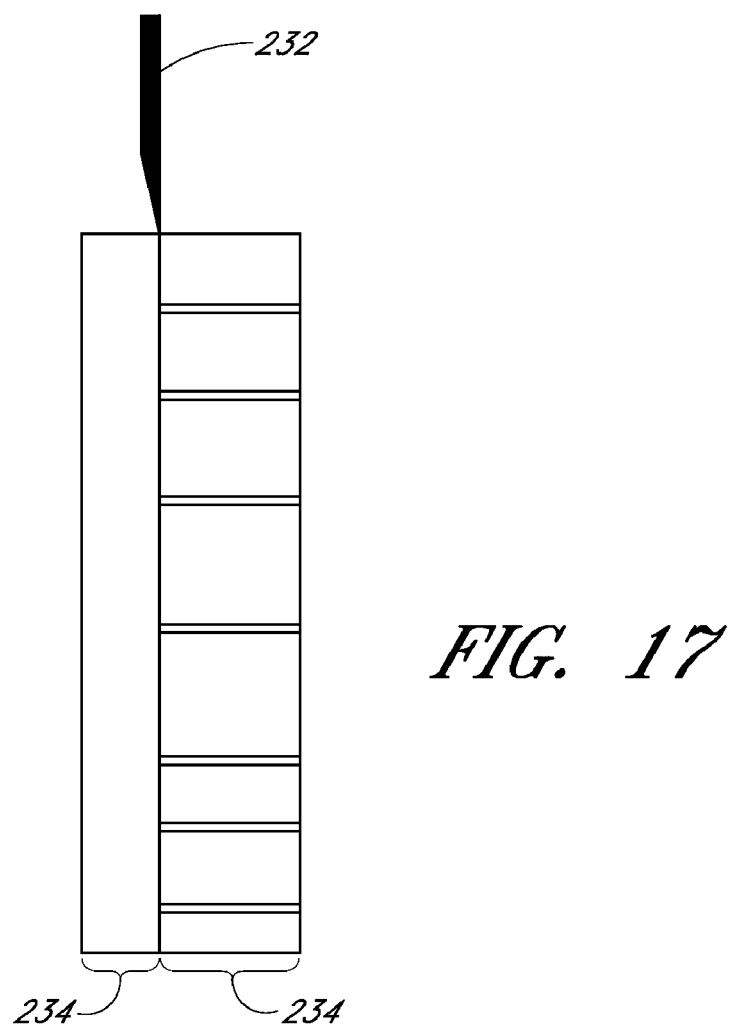
FIG. 17 is a cross-sectional view of the piezoelectric sheet of FIG. 16, illustrating a method of harvesting individual ultrasound radiating members.

Referring now to FIG. 17, in an exemplary embodiment, the individual ultrasound radiating members are harvested by using a dicing blade 232 or other precision cutting tool to separate uncut backside material 234 from the cut ultrasound radiating members 200. In one embodiment, illustrated in FIG. 17, the dicing blade 232 cuts at an angle that is substantially perpendicular to the longitudinal axis of the holes 216. In the exemplary embodiment illustrated in FIG. 17, the sheet 214 is placed upright, and is cut vertically downward, such that the cut ultrasound radiating members 200 can be caught and removed without being damaged by the dicing blade 232. In such embodiments, the dicing blade cut intersects the cuts 218 and the holes 216, thereby producing finished ultrasound radiating members as illustrated in FIGS. 12A through 12E.

The methods for manufacturing ultrasound radiating members disclosed herein have several advantages. For example, ultrasound radiating members having the configurations disclosed herein subject the piezoelectric material to reduced mechanical stresses during use, which decreases the likelihood of fracture and grain disruption as compared to conventionally manufactured ultrasound radiating members. Furthermore, the polygonal ultrasound radiating members described herein emit ultrasonic energy around a larger effective area, and with an improved output pattern, as compared to conventional cylindrical ultrasound radiating members. The methods disclosed herein are also less complex and less expensive than conventional machining methods. These methods are also particularly useful for manufacturing miniaturized ultrasonic elements.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used to manufacture non-piezoelectric components, and yet remain within the scope of the present invention. Thus, the present invention is to be limited only by the following claims.

I claim:

1. A method for manufacturing an ultrasonic catheter comprising:
   providing a sheet of piezoelectric material;
   drilling a plurality of holes into the piezoelectric material, each hole having an inner surface;
   making a plurality of cuts into the sheet, each cut having a depth less than the depth of the holes, the cuts forming an elongate polygon that is generally centered about one of the holes, the polygon having an outer surface;
   plating at least a portion of the inner and outer surfaces with a conductive material;
   cutting a backside from the sheet so as to separate a plurality of individual elongate piezoelectric polygons; and
   disposing at least one of the individual elongate piezoelectric polygons within a tubular catheter body.

2. The method of claim 1, wherein the backside is cut substantially parallel to a top surface of the sheet of piezoelectric material.

3. The method of claim 1, wherein the holes are cut through the piezoelectric material.

4. The method of claim 1, wherein the holes are blind holes that do not pass through the piezoelectric material.

5. The method of claim 1, wherein a plurality of elongate piezoelectric polygons are mounted on a central core configured to be disposed within the tubular catheter body.

6. The method of claim 5, further comprising electrically connecting the piezoelectric polygons in series.

7. The method of claim 1, wherein a plurality of elongate piezoelectric polygons are mounted on an electrically conductive central core configured to be disposed within the tubular catheter body.

* * * * *